US012629208B2

(12) United States Patent
Amos et al.

(10) Patent No.: US 12,629,208 B2
(45) Date of Patent: May 19, 2026

(54) DIGITAL TWIN OF ATRIA FOR ATRIAL FIBRILLATION PATIENTS

(71) Applicant: Biosense Webster (Israel) Ltd., Yokneam (IL)

(72) Inventors: Yariv Avraham Amos, Tzorit (IL); Matityahu Amit, Cohav-Yair zur-Yigal (IL); Liat Tsoref, Tel Aviv (IL)

(73) Assignee: BIOSENSE WEBSTER (ISRAEL) LTD., Yokneam (IL)

( * ) Notice: Subject to any disclaimer, the term of this patent is extended or adjusted under 35 U.S.C. 154(b) by 875 days.

(21) Appl. No.: 17/962,905

(22) Filed: Oct. 10, 2022

(65) Prior Publication Data

US 2023/0146716 A1     May 11, 2023

Related U.S. Application Data

(60) Provisional application No. 63/255,614, filed on Oct. 14, 2021.

(51) Int. Cl.
A61B 34/10        (2016.01)
A61B 5/341        (2021.01)
(Continued)

(52) U.S. Cl.
CPC .............. A61B 34/10 (2016.02); A61B 5/341 (2021.01); A61B 5/364 (2021.01); G16H 20/40 (2018.01);
(Continued)

(58) Field of Classification Search
CPC ......... A61B 34/10; A61B 5/364; A61B 5/341;

A61B 2034/105; A61B 2034/107; A61B 18/1492; A61B 2034/101; A61B 34/20; A61B 2034/2051; A61B 2034/2053; A61B 2034/2072; A61B 34/25; A61B 2017/00053; A61B 2018/00267; A61B 2018/00351; A61B 2018/00577;
(Continued)

(56) References Cited

U.S. PATENT DOCUMENTS 5,391,199 A     2/1995  Ben-Haim
5,443,489 A     8/1995  Ben-Haim
(Continued)

OTHER PUBLICATIONS

Cantwell, C. D. et al., "Rethinking multiscale cardiac electrophysiology with machine learning and predictive modelling," Comput. Biol. Med. 104, 339-351 (2019).
(Continued)

*Primary Examiner* — Shirley X Jian
(74) *Attorney, Agent, or Firm* — Volpe Koenig

(57)        ABSTRACT

An ablation procedure guidance method is provided herein. The ablation procedure guidance method is implemented by a generation engine executing on a processor. The ablation procedure guidance method includes receiving inputs including images and conduction velocity vector estimations and generating a digital twin of an anatomical structure utilizing the images and the conduction velocity vector estimations. The ablation procedure guidance method also includes presenting, via a user interface of the generation engine, the digital twin to provide precision ablation guidance of the anatomical structure and provide electrophysiology information of the anatomical structure.

19 Claims, 14 Drawing Sheets

(51) Int. Cl.

| | | |
|---|---|---|
| *A61B 5/364* | (2021.01) | |
| *G16H 20/40* | (2018.01) | |
| *G16H 50/50* | (2018.01) | |

(52) U.S. Cl.

CPC ........ *G16H 50/50* (2018.01); *A61B 2034/105* (2016.02); *A61B 2034/107* (2016.02)

(58) Field of Classification Search

CPC .. A61B 2018/00839; A61B 2018/1467; G16H 20/40; G16H 50/50; G16H 50/70; G16H 50/20; G16H 30/40; G06N 7/01; G06N 3/045

See application file for complete search history.

(56) References Cited

U.S. PATENT DOCUMENTS

| | | | | |
|---|---|---|---|---|
| 5,558,091 | A | 9/1996 | Acker et al. | |
| 6,172,499 | B1 | 1/2001 | Ashe | |
| 6,239,724 | B1 | 5/2001 | Doron et al. | |
| 6,332,089 | B1 | 12/2001 | Acker et al. | |
| 6,484,118 | B1 | 11/2002 | Govari | |
| 6,618,612 | B1 | 9/2003 | Acker et al. | |
| 6,690,963 | B2 | 2/2004 | Ben-Haim et al. | |
| 6,788,967 | B2 | 9/2004 | Ben-Haim et al. | |
| 6,892,091 | B1 | 5/2005 | Ben-Haim et al. | |
| 7,536,218 | B2 | 5/2009 | Govari et al. | |
| 7,756,576 | B2 | 7/2010 | Levin | |
| 7,848,787 | B2 | 12/2010 | Osadchy | |
| 7,869,865 | B2 | 1/2011 | Govari et al. | |
| 8,456,182 | B2 | 6/2013 | Bar-tal et al. | |
| 11,350,867 | B2 * | 6/2022 | Gaeta | A61B 5/25 |
| 11,664,125 | B2 * | 5/2023 | Tuysuzoglu | G06N 3/08 |
| | | | | 600/428 |
| 11,911,095 | B2 * | 2/2024 | Shariat | A61B 5/333 |
| 12,156,701 | B2 * | 12/2024 | Shamilov | A61B 5/367 |
| 2017/0330075 | A1 * | 11/2017 | Tuysuzoglu | G06N 7/08 |
| 2019/0328258 | A1 * | 10/2019 | Gaeta | A61B 5/282 |
| 2020/0146579 | A1 * | 5/2020 | Bar-Tal | A61B 5/341 |
| 2021/0059549 | A1 | 3/2021 | Urman et al. | |
| 2021/0059550 | A1 | 3/2021 | Urman et al. | |
| 2021/0093217 | A1 * | 4/2021 | Shariat | A61B 5/361 |
| 2023/0109856 | A1 * | 4/2023 | Shamilov | A61B 5/367 |
| | | | | 606/34 |
| 2023/0149089 | A1 * | 5/2023 | Trayanova | G16H 20/40 |
| | | | | 705/2 |
| 2023/0181087 | A1 * | 6/2023 | Rodriguez | A61B 5/6858 |
| | | | | 600/523 |

OTHER PUBLICATIONS

Kirchhof, P. & Calkins, H., "Catheter ablation in patients with persistent atrial fibrillation," Eur. Heart J. 38, 20-26 (2017).

Verma, A. et al., "Characterization and significance of localized sources identified by a novel automated algorithm during mapping of human persistent atrial fibrillation," J. Cardiovasc. Electrophysiol. 29, 1480-1488 (2018).

Narayan, S. M. et al., "Treatment of Atrial Fibrillation by the Ablation of Localized Sources: CONFIRM (Conventional Ablation for Atrial Fibrillation With or Without Focal Impulse and Rotor Modulation)," Trial. J. Am. Coll. Cardiol. 60, 628-636 (2012).

Davidenko, J. M., Pertsov, A. V., Salomonsz, R., Baxter, W. & Jalife, J., "Stationary and drifting spiral waves of excitation in isolated cardiac muscle," Nature 355, 349-351 (1992).

Verheule, S. et al., "Role of endo-epicardial dissociation of electrical activity and transmural conduction in the development of persistent atrial fibrillation," Progress in Biophysics and Molecular Biology 115, 173-185 (2014).

Nademanee, K., Lockwood, E., Oketani, N. & Gidney, B., "Catheter ablation of atrial fibrillation guided by complex fractionated atrial electrogram mapping of atrial fibrillation substrate," J. Cardiol. 55, 1-12 (2010).

Sanders, P. et al., "Spectral analysis identifies sites of high-frequency activity maintaining atrial fibrillation in humans," Circulation 112, 789-797 (2005).

Verma, A. et al., "Approaches to Catheter Ablation for Persistent Atrial Fibrillation," N. Engl. J. Med. 372, 1812-1822 (2015).

Mihalef, V., Passerini, T. & Mansi, T., "Multi-scale models of the heart for patient-specific simulations," Artif. Intell. Comput. Model. Hear. 3-42 (2019).

Mansi, T., Passerini, T. & Comaniciu, D., "Artificial intelligence for computational modeling of the heart, " (2019).

Rapaka, S. et al., "LBM-EP: Lattice-boltzmann method for fast cardiac electrophysiology simulation from 3D images," Lect. Notes Comput. Sci. (including Subser. Lect. Notes Artif. Intell. Lect. Notes Bioinformatics) 7511 LNCS, 33-40 (2012).

* cited by examiner

1540

1510

Conduction Velocity (mV/msec)

0.21 0.45 0.70 0.94 1.19 1.43 1.68 1.92

DIGITAL TWIN OF ATRIA FOR ATRIAL FIBRILLATION PATIENTS

INCORPORATION BY REFERENCE

This application claims priority to U.S. Provisional Application No. 63/255,614, which was filed on Oct. 14, 2021, and is incorporated herein by reference in its entirety.

FIELD OF INVENTION

The present invention is related to signal processing. More particularly, the present invention relates to generating a digital twin of atria for atrial fibrillation (aFib) patients.

BACKGROUND

Cardiac arrhythmia, such as aFib, occurs when regions of cardiac tissue do not follow a synchronous beating cycle associated with normally conductive tissue. Generally, cardiac arrhythmia can be treated by medication, ablation or other means of tissue destruction. Yet, with respect to aFib in its advanced stages, knowing optimal locations for ablation becomes quite complicated. For instance, because aFib can vary from one patient to another and because atrial tissue can include scars and/or triggers, optimal ablation locations may need to be determined on a case by case basis.

Currently, ablation procedures construct and utilize digital simulations of a heart to assist with determining ablation locations. These digital simulations are based on standard anatomical information and assume a standard electrical conduction. Accordingly, it has been found that these simulations are not accurate enough and do not foster effective guidance. Thus, there is a need for improved ablation location determining techniques.

SUMMARY

According to an exemplary embodiment, an ablation procedure guidance method is provided herein. The ablation procedure guidance method is implemented by a generation engine executing on at least one processor. The ablation procedure guidance method includes receiving, by the generation engine, one or more inputs including one or more images and conduction velocity vector estimations. The ablation procedure guidance method also includes generating, by the generation engine, a digital twin of an anatomical structure utilizing the one or more images and the conduction velocity vector estimations. The ablation procedure guidance method also includes presenting, via a user interface of the generation engine, the digital twin to provide precision ablation guidance of the anatomical structure and provide electrophysiology information of the anatomical structure.

According to one or more embodiments, the above ablation procedure guidance method can be implemented as a system, an apparatus, and/or a computer program product.

BRIEF DESCRIPTION OF THE DRAWINGS

A more detailed understanding may be had from the following description, given by way of example in conjunction with the accompanying drawings, wherein like reference numerals in the figures indicate like elements, and wherein.

DETAILED DESCRIPTION

Figure 1:
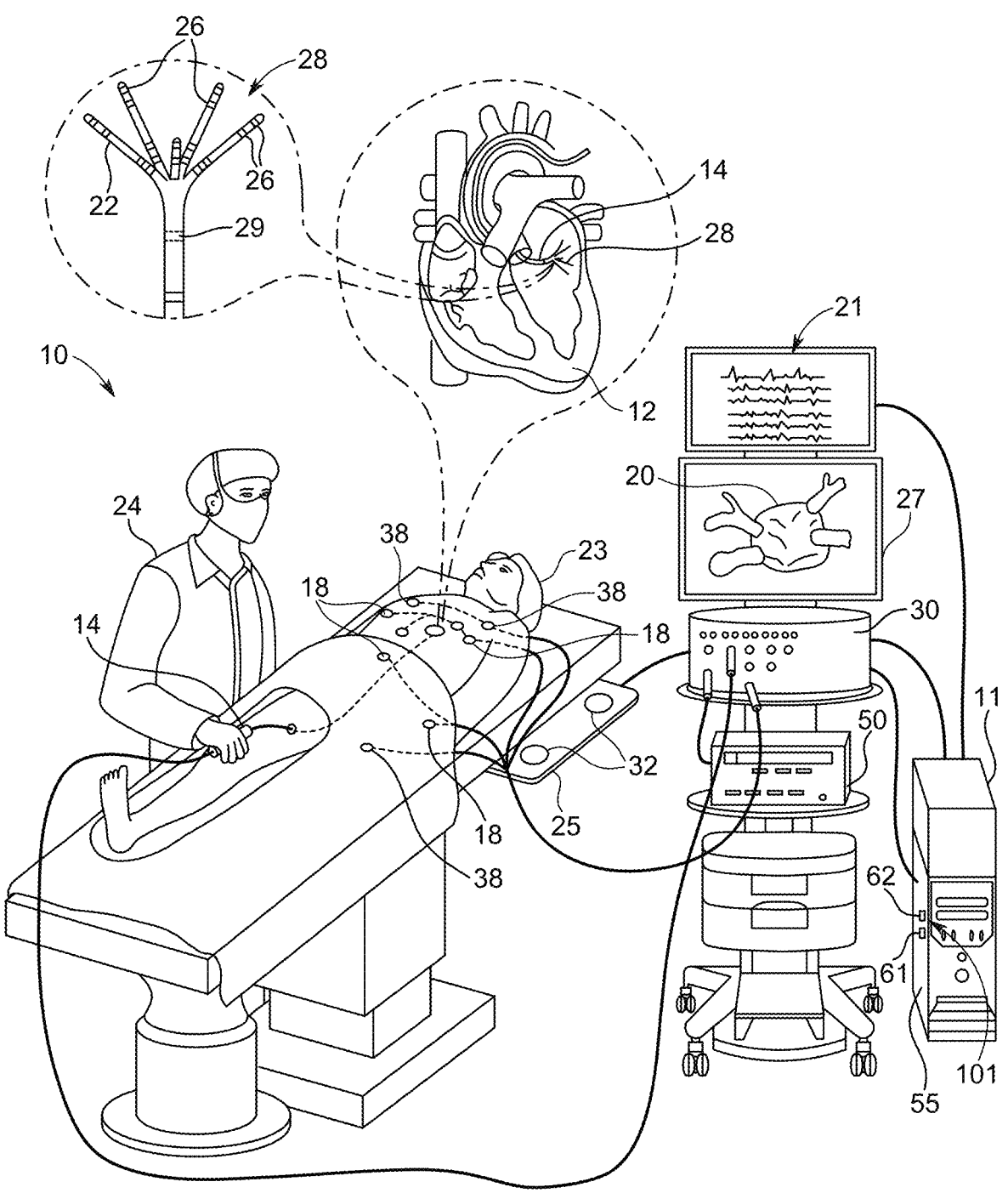
FIG. 1 illustrates a diagram of an example system in which one or more features of the disclosure subject matter can be implemented according to one or more embodiments.

Disclosed herein is a signal processing system, apparatus, and method. More particularly, disclosed herein are signal processing operations that generate a digital twin of atria for atrial fibrillation (aFib) patients. The signal processing systems, apparatus, and method can incorporate a machine learning (ML) and/or an artificial intelligence (AI) to generate and analyze the digital twin, as well as data associated therewith, to provide improved ablation location determining techniques.

According to one or more embodiments, a generation engine can generally correspond to the signal processing systems, apparatus, and method and include one or more ML/AI algorithms to generate and analyze the digital twin. In this regard, the generation engine can include a processor executable code or software that is necessarily rooted in process operations by, and in processing hardware of, medical device equipment. For ease of explanation, the generation engine is described herein with respect to mapping a heart (such as an atria thereof). However, any anatomical structure, body part, organ, or portion thereof can be a target for mapping by the generation engine described herein.

In general, the generation engine generates/creates the digital twin of the atria to serve as a guiding tool for ablations of aFib patients. Particularly, the digital twin is more robust than current digital simulations, which do not have personalized electrical activity of the heart, i.e., the digital simulations assume a standard electrical conduction and assume that arrythmias repeat themselves, which is not the case in aFib. In this regard, for example, the generation engine measures and utilizes electrical activity of the heart (e.g., while accounting for arrhythmia triggers, as well as information regarding atrial wall substances) for an aFib patient to generate and create the digital twin. By way of further example, the generation engine utilizes conduction velocity (CV) vectors (e.g., a direct heart measurement) as input to generate and create the digital twin. The CV vectors can be based on real-time data, as described herein. The CV vectors are based on the local signal progress; therefore, the generation engine can utilize far field reduction algorithms to remove a far field (i.e., signal that is based on the ventricle activation) before calculating the CV vectors. Additionally, during an ablation procedure, the generation engine can continuous update the digital twin, as well as suggest an optimal ablation and/or additional procedures based on the digital twin.

As a result of the operations of the generation engine, the digital twin is very accurate compared to current digital simulations. Thus, one or more advantages, technical effects, and/or benefits of the generation engine can include providing cardiac physicians and medical personnel with effective guidance during ablation procedures using the digital twin. In turn, the generation engine particularly utilizes and transforms medical device equipment to enable/implement signal processing operations that are otherwise not currently available or currently performed by cardiac physicians and medical personnel.

FIG. 1 is a diagram of an example system (e.g., medical device equipment and/or catheter-based electrophysiology mapping and ablation), shown as a system 10, in which one or more features of the subject matter herein can be implemented according to one or more embodiments. All or part of the system 10 can be used to collect information (e.g., biometric data and/or a training dataset) and/or used to implement a ML/AI algorithm and far field reduction algorithms (e.g., of a generation engine 101) as described herein. The system 10, as illustrated, includes a recorder 11, a heart 12, a catheter 14, a model or anatomical map 20, an electrogram 21, a spline 22, a patient 23, a physician 24 (or a medical professional or clinician), a location pad 25, an electrode 26, a display device 27, a distal tip 28, a sensor 29, a coil 32, a patient interface unit (PIU) 30, electrode skin patches 38, an ablation energy generator 50, and a workstation 55 (including at least one processor 61 and at least one memory 62, storing a generation engine 101 therein). Note that each element and/or item of the system 10 is representative of one or more of that element and/or that item. The example of the system 10 shown in FIG. 1 can be modified to implement the embodiments disclosed herein. The disclosed embodiments can similarly be applied using other system components and settings. Additionally, the system 10 can include additional components, such as elements for sensing electrical activity, wired or wireless connectors, processing and display devices, or the like.

The system 10 includes multiple catheters 14, which are percutaneously inserted by the physician 24 through the patient's 23 vascular system into a chamber or vascular structure of the heart 12. Typically, a delivery sheath catheter (which is an example of the catheter 14) is inserted into the left or right atrium near a desired location in the heart 12. Thereafter, a plurality of catheters 14 can be inserted into the delivery sheath catheter so as to arrive at the desired location. The plurality of catheters 14 may include catheters dedicated for sensing Intracardiac Electrogram (IEGM) signals, catheters dedicated for ablating and/or catheters dedicated for both sensing and ablating. The example catheter 14 that is configured for sensing IEGM is illustrated herein. The physician 24 brings the distal tip 28 of the catheter 14 into contact with the heart wall for sensing a target site in the heart 12. For ablation, the physician 24 would similarly bring a distal end of an ablation catheter to a target site for ablating.

The catheter 14 is an exemplary catheter that includes one and preferably multiple electrodes 26 optionally distributed over a plurality of splines 22 at the distal tip 28 and configured to sense the IEGM signals. The catheter 14 may additionally include the sensor 29 embedded in or near the distal tip 28 for tracking position and orientation of the distal tip 28. Optionally and preferably, position sensor 29 is a magnetic based position sensor including three magnetic coils for sensing three-dimensional (3D) position and orientation.

The sensor 29 (e.g., a position or a magnetic based position sensor) may be operated together with the location pad 25 including a plurality of magnetic coils 32 configured to generate magnetic fields in a predefined working volume. Real time position of the distal tip 28 of the catheter 14 may be tracked based on magnetic fields generated with the location pad 25 and sensed by the sensor 29. Details of the magnetic based position sensing technology are described in U.S. Pat. Nos. 5,5391,199; 5,443,489; 5,558,091; 6,172,499; 6,239,724; 6,332,089; 6,484,118; 6,618,612; 6,690,963; 6,788,967; 6,892,091.

The system 10 includes one or more electrode patches 38 positioned for skin contact on the patient 23 to establish location reference for the location pad 25 as well as impedance-based tracking of the electrodes 26. For impedance-based tracking, electrical current is directed toward the electrodes 26 and sensed at the patches 38 (e.g., electrode skin patches) so that the location of each electrode can be triangulated via the patches 38. Details of the impedance-based location tracking technology are described in U.S. Pat. Nos. 7,536,218; 7,756,576; 7,848,787; 7,869,865; and 8,456,182, which are incorporated herein by reference.

The recorder 11 displays the electrograms 21 captured with the electrodes 18 (e.g., body surface electrocardiogram (ECG) electrodes) and IEGM captured with the electrodes 26 of the catheter 14. The recorder 11 may include pacing capability for pacing the heart rhythm and/or may be electrically connected to a standalone pacer.

The system 10 may include the ablation energy generator 50 that is adapted to conduct ablative energy to the one or more of electrodes 26 at the distal tip 28 of the catheter 14 configured for ablating. Energy produced by the ablation energy generator 50 may include, but is not limited to, radiofrequency (RF) energy or pulsed-field ablation (PFA) energy, including monopolar or bipolar high-voltage DC pulses as may be used to effect irreversible electroporation (IRE), or combinations thereof.

The PIU 30 is an interface configured to establish electrical communication between catheters, electrophysiological equipment, power supply and the workstation 55 for controlling operation of the system 10. Electrophysiological equipment of the system 10 may include for example, multiple catheters 14, the location pad 25, the body surface ECG electrodes 18, the electrode patches 38, the ablation energy generator 50, and the recorder 11. Optionally and preferably, the PIU 30 additionally includes processing capability for implementing real-time computations of location of the catheters and for performing ECG calculations.

The workstation 55 includes the memory 62, the processor unit 61 with the memory 62 or storage with appropriate operating software loaded therein, and user interface capability, as further described herein. The workstation 55 may provide multiple functions, optionally including (1) modeling the endocardial anatomy in three-dimensions (3D) and rendering the model or anatomical map 20 for display on the display device 27, (2) displaying on the display device 27 activation sequences (or other data) compiled from recorded electrograms 21 in representative visual indicia or imagery superimposed on the rendered anatomical map 20, (3) displaying real-time location and orientation of multiple catheters within the heart chamber, and (5) displaying on the display device 27 sites of interest such as places where ablation energy has been applied. One commercial product embodying elements of the system 10 is available as the CARTO® 3 System, available from Biosense Webster, Inc., 31A Technology Drive, Irvine, CA 92618.

The system 10 can be utilized to detect, diagnose, and/or treat cardiac conditions (e.g., using the generation engine 101). Cardiac conditions, such as cardiac arrhythmias, persist as common and dangerous medical ailments, especially in the aging population. For instance, the system 10 can be part of a surgical system (e.g., CARTO® system sold by Biosense Webster) that is configured to obtain biometric data (e.g., anatomical and electrical measurements of a patient's organ, such as the heart 12 and as described herein) and perform a cardiac ablation procedure. More particularly, treatments for cardiac conditions such as cardiac arrhythmia often require obtaining a detailed mapping of cardiac tissue, chambers, veins, arteries and/or electrical pathways. For example, a prerequisite for performing a catheter ablation (as described herein) successfully is that the cause of the cardiac arrhythmia is accurately located in a chamber of the heart 12. Such locating may be done via an electrophysiological investigation during which electrical potentials are detected spatially resolved with a mapping catheter (e.g., the catheter 14) introduced into the chamber of the heart 12. This electrophysiological investigation, the so-called electro-anatomical mapping, thus provides 3D mapping data which can be displayed on the display device 27. In many cases, the mapping function and a treatment function (e.g., ablation) are provided by a single catheter or group of catheters such that the mapping catheter also operates as a treatment (e.g., ablation) catheter at the same time.

In patients (e.g., the patient 23) with normal sinus rhythm (NSR), the heart (e.g., the heart 12), which includes atrial, ventricular, and excitatory conduction tissue, is electrically excited to beat in a synchronous, patterned fashion. Note that this electrical excitement can be detected as intracardiac electrocardiogram (IC ECG) data or the like.

According to one or more embodiment, in patients (e.g., the patient 23) with a cardiac arrhythmia (e.g., atrial fibrillation or aFib), abnormal regions of cardiac tissue do not follow a synchronous beating cycle associated with normally conductive tissue, which is in contrast to patients with NSR. Instead, the abnormal regions of cardiac tissue aberrantly conduct to adjacent tissue, thereby disrupting the cardiac cycle into an asynchronous cardiac rhythm. Note that this asynchronous cardiac rhythm can also be detected as the IC ECG data. Such abnormal conduction has been previously known to occur at various regions of the heart 12, for example, in the region of the sino-atrial (SA) node, along the conduction pathways of the atrioventricular (AV) node, or in the cardiac muscle tissue forming the walls of the ventricular and atrial cardiac chambers. There are other conditions, such as flutter, where the pattern of abnormally conducting tissues lead to reentry paths such that the chamber beats in a regular pattern that can be multiple times the sinus rhythm.

By way of example, in support of the system 10 detecting, diagnosing, and/or treating cardiac conditions, the catheter 14 can be navigated by the physician 24 into the heart 12 of the patient 23 lying on the bed. For instance, the physician 24 can insert the shaft through the sheath, while manipulating a distal end of the shaft using the manipulator near the proximal end of the catheter 14 and/or deflection from the sheath. According to one or more embodiments, the catheter 14 can be fitted at the distal end of the shaft. The catheter 14 can be inserted through the sheath in a collapsed state and can be then expanded within the heart 12.

Generally, electrical activity at a point in the heart 12 may be typically measured by advancing the catheter 14 containing an electrical sensor (e.g., the sensor 29) at or near its distal tip (e.g., the at least one electrode 26) to that point in the heart 12, contacting the tissue with the sensor and acquiring data at that point. One drawback with mapping a cardiac chamber using a catheter type containing only a single, distal tip electrode is the long period of time required to accumulate data on a point-by-point basis over the requisite number of points required for a detailed map of the chamber as a whole. Accordingly, multiple-electrode catheters (e.g., the catheter 14) have been developed to simultaneously measure electrical activity at multiple points in the heart chamber.

The catheter 14, which can include the at least one electrode 26 and a catheter needle coupled onto a body thereof, can be configured to obtain biometric data, such as electrical signals of an intra-body organ (e.g., the heart 12), and/or to ablate tissue areas of thereof (e.g., a cardiac chamber of the heart 12). Note that the electrodes 26 are representative of any like elements, such as tracking coils, piezoelectric transducer, electrodes, or combination of elements configured to ablate the tissue areas or to obtain the biometric data. According to one or more embodiments, the catheter 14 can include one or more position sensors that used are to determine trajectory information. The trajectory information can be used to infer motion characteristics, such as the contractility of the tissue.

Biometric data (e.g., patient biometrics, patient data, or patient biometric data) can include one or more of local activation times (LATs), electrical activity, topology, bipolar mapping, reference activity, ventricle activity, dominant frequency, impedance, or the like. The LAT can be a point in time of a threshold activity corresponding to a local activation, calculated based on a normalized initial starting point. Electrical activity can be any applicable electrical signals that can be measured based on one or more thresholds and can be sensed and/or augmented based on signal to noise ratios and/or other filters. A topology can correspond to the physical structure of a body part or a portion of a body part and can correspond to changes in the physical structure relative to different parts of the body part or relative to different body parts. A dominant frequency can be a frequency or a range of frequency that is prevalent at a portion of a body part and can be different in different portions of the same body part. For example, the dominant frequency of a PV of a heart can be different than the dominant frequency of the right atrium of the same heart. Impedance can be the resistance measurement at a given area of a body part.

Examples of biometric data include, but are not limited to, patient identification data, IC ECG data, bipolar intracardiac reference signals, anatomical and electrical measurements, trajectory information, body surface (BS) ECG data, historical data, brain biometrics, blood pressure data, ultrasound signals, radio signals, audio signals, a two- or three-dimensional (3D) image data, blood glucose data, and temperature data. The biometrics data can be used, generally, to monitor, diagnosis, and treatment any number of various diseases, such as cardiovascular diseases (e.g., arrhythmias, cardiomyopathy, and coronary artery disease) and autoimmune diseases (e.g., type I and type II diabetes). Note that BS ECG data can include data and signals collected from electrodes on a surface of a patient, IC ECG data can include data and signals collected from electrodes within the patient, and ablation data can include data and signals collected from tissue that has been ablated. Further, BS ECG data, IC ECG data, and ablation data, along with catheter electrode position data, can be derived from one or more procedure recordings.

For example, the catheter 14 can use the electrodes 26 to implement intravascular ultrasound and/or MRI catheterization to image the heart 12 (e.g., obtain and process the biometric data). The catheter 14 is shown in an enlarged view, inside a cardiac chamber of the heart 12. It will be understood that any shape that includes one or more electrodes 26 can be used to implement the embodiments disclosed herein.

Examples of the catheter 14 include, but are not limited to, a linear catheter with multiple electrodes, a balloon catheter including electrodes dispersed on multiple spines that shape the balloon, a lasso, a catheter with electrodes in shape of a grid or loop catheter with multiple electrodes, a high density catheter, or any other applicable shape or complexity. Linear catheters can be fully or partially elastic such that it can twist, bend, and or otherwise change its shape based on received signal and/or based on application of an external force (e.g., cardiac tissue) on the linear catheter. The balloon catheter can be designed such that when deployed into a patient's body, its electrodes can be held in intimate contact against an endocardial surface. As an example, a balloon catheter can be inserted into a lumen, such as a pulmonary vein (PV). The balloon catheter can be inserted into the PV in a deflated state, such that the balloon catheter does not occupy its maximum volume while being inserted into the PV. The balloon catheter can expand while inside the PV, such that those electrodes on the balloon catheter are in contact with an entire circular section of the PV. Such contact with an entire circular section of the PV, or any other lumen, can enable efficient imaging and/or ablation. Other examples of the catheter 14 include PentaRay® catheter and Constellation catheter.

According to other examples, body patches and/or body surface electrodes (e.g., the one or more electrode patches 38) may also be positioned on or proximate to a body of the patient 23. The catheter 14 with the one or more electrodes 26 can be positioned within the body (e.g., within the heart 12) and a position of the catheter 14 can be determined by the 100 system based on signals transmitted and received between the one or more electrodes 26 of the catheter 14 and the body patches and/or body surface electrodes. Additionally, the electrodes 26 can sense the biometric data from within the body of the patient 23, such as within the heart 12 (e.g., the electrodes 26 sense the electrical potential of the tissue in real time). The biometric data can be associated with the determined position of the catheter 14 such that a rendering of the patient's body part (e.g., the heart 12) can be displayed and show the biometric data overlaid on a shape of the body part.

By way of further example, the catheter 14 and other items of the system 10 can be connected to the workstation 55. The workstation 55 can include any computing device, which employs the ML/AI algorithm (which can be included within the generation engine 101). According to an exemplary embodiment, the workstation 55 includes the one or more processors 61 (any computing hardware) and the memory 62 (any non-transitory tangible media), where the one or more processors 61 execute computer instructions with respect the generation engine 101 and the memory 62 stores these instructions for execution by the one or more processors 61. For instance, the workstation 55 can be configured to receive and process the biometric data and determine if a given tissue area conducts electricity. In some embodiments, the workstation 55 can be further programmed by the generation engine 101 (in software) to carry out the functions of an ablation procedure guidance method. For example, the ablation procedure guidance method can include receiving inputs (e.g., including one or more images and conduction velocity vector estimations), generating a digital twin of an anatomical structure utilizing the images and the conduction velocity vector estimations, and presenting the digital twin to provide precision ablation guidance of the anatomical structure and provide electrophysiology information of the anatomical structure.

According to one or more embodiments, the generation engine 101 can be external to the workstation 55 and can be located, for example, in the catheter 14, in an external device, in a mobile device, in a cloud-based device, or can be a standalone processor. In this regard, the generation engine 101 can be transferable/downloaded in electronic form, over a network.

In an example, the workstation 55 can be any computing device, as noted herein, including software (e.g., the generation engine 101) and/or hardware (e.g., the processor 61 and the memory 62), such as a general-purpose computer, with suitable front end and interface circuits for transmitting and receiving signals to and from the catheter 14, as well as for controlling the other components of the system 10. For example, the front end and interface circuits include input/output (I/O) communication interfaces that enables the workstation 55 to receive signals from and/or transfer signals to the at least one electrode 26. The workstation 55 can include real-time noise reduction circuitry typically configured as a field programmable gate array (FPGA), followed by an analog-to-digital (A/D) ECG or electrocardiograph/electromyogram (EMG) signal conversion integrated circuit. The workstation 55 can pass the signal from an A/D ECG or EMG circuit to another processor and/or can be programmed to perform one or more functions disclosed herein.

The display device 27, which can be any electronic device for the visual presentation of the biometric data, is connected to the workstation 55. According to an exemplary embodiment, during a procedure, the workstation 55 can facilitate on the display device 27 a presentation of a body part rendering to the physician 24 and store data representing the body part rendering in the memory 62. For instance, maps depicting motion characteristics can be rendered/constructed based on the trajectory information sampled at a sufficient number of points in the heart 12. As an example, the display device 27 can include a touchscreen that can be configured to accept inputs from the medical professional 115, in addition to presenting the body part rendering.

In some embodiments, the physician 24 may manipulate the elements of the system 10 and/or the body part rendering using one or more input devices, such as a touch pad, a mouse, a keyboard, a gesture recognition apparatus, or the like. For example, an input device can be used to change a position of the catheter 14, such that rendering is updated. Note that the display device 27 can be located at a same location or a remote location, such as a separate hospital or in separate healthcare provider networks.

According to one or more embodiments, the system 10 can also obtain the biometric data using ultrasound, computed tomography (CT), MRI, or other medical imaging techniques utilizing the catheter 14 or other medical equipment. For instance, the system 10 can obtain ECG data and/or anatomical and electrical measurements of the heart 12 (e.g., the biometric data) using one or more catheters 14 or other sensors. More particularly, the workstation 55 can be connected, by a cable, to BS electrodes, which include adhesive skin patches affixed to the patient 23. The BS electrodes can procure/generate the biometric data in the form of the BS ECG data. For instance, the processor 61 can determine position coordinates of the catheter 14 inside the body part (e.g., the heart 12) of the patient 23. The position coordinates may be based on impedances or electromagnetic fields measured between the body surface electrodes and the electrode 26 of the catheter 14 or other electromagnetic components. Additionally, or alternatively, location pads, which generate magnetic fields used for navigation, may be located on a surface of a bed (or a table). and may be separate from the bed. The biometric data can be transmitted to the workstation 55 and stored in the memory 62. Alternatively, or in addition, the biometric data may be transmitted to a server, which may be local or remote, using a network as further described herein.

According to one or more embodiments, the catheter 14 may be configured to ablate tissue areas of a cardiac chamber of the heart 12. For instance, the catheter 14, in an enlarged view, inside a cardiac chamber of the heart 12. Further, ablation electrodes, such as the at least one electrode 26, may be configured to provide energy to tissue areas of an intra-body organ (e.g., the heart 12). The energy may be thermal energy and may cause damage to the tissue area starting from the surface of the tissue area and extending into the thickness of the tissue area. The biometric data with respect to ablation procedures (e.g., ablation tissues, ablation locations, etc.) can be considered ablation data.

According to an example, with respect to obtaining the biometric data, a multi-electrode catheter (e.g., the catheter 14) can be advanced into a chamber of the heart 12. Anteroposterior (AP) and lateral fluorograms can be obtained to establish the position and orientation of each of the electrodes. ECGs can be recorded from each of the electrodes 26 in contact with a cardiac surface relative to a temporal reference, such as the onset of the P-wave in sinus rhythm from a BS ECG and/or signals from electrodes 26 of the catheter 14 placed in the coronary sinus. The system, as further disclosed herein, may differentiate between those electrodes that register electrical activity and those that do not due to absence of close proximity to the endocardial wall. After initial ECGs are recorded, the catheter may be repositioned, and fluorograms and ECGs may be recorded again. An electrical map (e.g., via cardiac mapping) can then be constructed from iterations of the process above.

Cardiac mapping can be implemented using one or more techniques. Generally, mapping of cardiac areas such as cardiac regions, tissue, veins, arteries and/or electrical pathways of the heart 12 may result in identifying problem areas such as scar tissue, arrhythmia sources (e.g., electric rotors), healthy areas, and the like. Cardiac areas may be mapped such that a visual rendering of the mapped cardiac areas is provided using a display, as further disclosed herein. Additionally, cardiac mapping (which is an example of heart imaging) may include mapping based on one or more modalities such as, but not limited to LAT, local activation velocity, an electrical activity, a topology, a bipolar mapping, a dominant frequency, or an impedance. Data (e.g., biometric data) corresponding to multiple modalities may be captured using a catheter (e.g., the catheter 14) inserted into a patient's body and may be provided for rendering at the same time or at different times based on corresponding settings and/or preferences of the physician 24.

As an example of a first technique, cardiac mapping may be implemented by sensing an electrical property of heart tissue, for example, LAT, as a function of the precise location within the heart 12. The corresponding data (e.g., biometric data) may be acquired with one or more catheters (e.g., the catheter 14) that are advanced into the heart 12 and that have electrical and location sensors (e.g., the electrodes 26) in their distal tips. As specific examples, location and electrical activity may be initially measured on about 10 to about 20 points on the interior surface of the heart 12. These data points may be generally sufficient to generate a preliminary reconstruction or map of the cardiac surface to a satisfactory quality. The preliminary map may be combined with data taken at additional points to generate a more comprehensive map of the heart's electrical activity. In clinical settings, it is not uncommon to accumulate data at 100 or more sites (e.g., several thousand) to generate a detailed, comprehensive map of heart chamber electrical activity. The generated detailed map may then serve as the basis for deciding on a therapeutic course of action, for example, tissue ablation as described herein, to alter the propagation of the heart's electrical activity and to restore normal heart rhythm.

Further, cardiac mapping can be generated based on detection of intracardiac electrical potential fields (e.g., which is an example of IC ECG data and/or bipolar intracardiac reference signals). A non-contact technique to simultaneously acquire a large amount of cardiac electrical information may be implemented. For example, a catheter type having a distal end portion may be provided with a series of sensor electrodes distributed over its surface and connected to insulated electrical conductors for connection to signal sensing and processing means. The size and shape of the end portion may be such that the electrodes are spaced substantially away from the wall of the cardiac chamber. Intracardiac potential fields may be detected during a single cardiac beat. According to an example, the sensor electrodes may be distributed on a series of circumferences lying in planes spaced from each other. These planes may be perpendicular to the major axis of the end portion of the catheter. At least two additional electrodes may be provided adjacent at the ends of the major axis of the end portion. As a more specific example, the catheter may include four circumferences with eight electrodes spaced equiangularly on each circumference. Accordingly, in this specific implementation, the catheter may include at least 34 electrodes (32 circumferential and 2 end electrodes). As another more specific example, the catheter may include other multi-spline catheters, such as five soft flexible branches, eight radial splines, or a parallel splined pancake turner type (e.g., any of which may have a total of 42 electrodes).

As example of electrical or cardiac mapping, an electrophysiological cardiac mapping system and technique based on a non-contact and non-expanded multi-electrode catheter (e.g., the catheter 14) can be implemented. ECGs may be obtained with one or more catheters 14 having multiple electrodes (e.g., such as between 42 to 122 electrodes). According to this implementation, knowledge of the relative geometry of the probe and the endocardium can be obtained by an independent imaging modality, such as transesophageal echocardiography. After the independent imaging, non-contact electrodes may be used to measure cardiac surface potentials and construct maps therefrom (e.g., in some cases using bipolar intracardiac reference signals). This technique can include the following steps (after the independent imaging step): (a) measuring electrical potentials with a plurality of electrodes disposed on a probe positioned in the heart 12; (b) determining the geometric relationship of the probe surface and the endocardial surface and/or other reference; (c) generating a matrix of coefficients representing the geometric relationship of the probe surface and the endocardial surface; and (d) determining endocardial potentials based on the electrode potentials and the matrix of coefficients.

As another example of electrical or cardiac mapping, a technique and apparatus for mapping the electrical potential distribution of a heart chamber can be implemented. An intra-cardiac multi-electrode mapping catheter assembly can be inserted into the heart 12. The mapping catheter (e.g., the catheter 14) assembly can include a multi-electrode array with one or more integral reference electrodes (e.g., one or the electrodes 26) or a companion reference catheter.

According to one or more embodiments, the electrodes may be deployed in the form of a substantially spherical array, which may be spatially referenced to a point on the endocardial surface by the reference electrode or by the reference catheter this is brought into contact with the endocardial surface. The preferred electrode array catheter may carry a number of individual electrode sites (e.g., at least 24). Additionally, this example technique may be implemented with knowledge of the location of each of the electrode sites on the array, as well as knowledge of the cardiac geometry. These locations are preferably determined by a technique of impedance plethysmography.

In view of electrical or cardiac mapping and according to another example, the catheter 14 can be a heart mapping catheter assembly that may include an electrode array defining a number of electrode sites. The heart mapping catheter assembly can also include a lumen to accept a reference catheter having a distal tip electrode assembly that may be used to probe the heart wall. The map heart mapping catheter assembly can include a braid of insulated wires (e.g., having 24 to 64 wires in the braid), and each of the wires may be used to form electrode sites. The heart mapping catheter assembly may be readily positionable in the heart 12 to be used to acquire electrical activity information from a first set of non-contact electrode sites and/or a second set of in-contact electrode sites.

Further, according to another example, the catheter 14 that can implement mapping electrophysiological activity within the heart can include a distal tip that is adapted for delivery of a stimulating pulse for pacing the heart or an ablative electrode for ablating tissue in contact with the tip. This catheter 14 can further include at least one pair of orthogonal electrodes to generate a difference signal indicative of the local cardiac electrical activity adjacent the orthogonal electrodes.

As noted herein, the system 10 can be utilized to detect, diagnose, and/or treat cardiac conditions. In example operation, a process for measuring electrophysiologic data in a heart chamber may be implemented by the system 10. The process may include, in part, positioning a set of active and passive electrodes into the heart 12, supplying current to the active electrodes, thereby generating an electric field in the heart chamber, and measuring the electric field at the passive electrode sites. The passive electrodes are contained in an array positioned on an inflatable balloon of a balloon catheter. In preferred embodiments, the array is said to have from 60 to 64 electrodes.

As another example operation, cardiac mapping may be implemented by the system 10 using one or more ultrasound transducers. The ultrasound transducers may be inserted into a patient's heart 12 and may collect a plurality of ultrasound slices (e.g., two dimensional or 3D slices) at various locations and orientations within the heart 12. The location and orientation of a given ultrasound transducer may be known and the collected ultrasound slices may be stored such that they can be displayed at a later time. One or more ultrasound slices corresponding to the position of the catheter 14 (e.g., a treatment catheter) at the later time may be displayed and the catheter 14 may be overlaid onto the one or more ultrasound slices.

In view of the system 10, it is noted that cardiac arrhythmias, including atrial arrhythmias, may be of a multiwavelet reentrant type, characterized by multiple asynchronous loops of electrical impulses that are scattered about the atrial chamber and are often self-propagating (e.g., another example of the IC ECG data). Alternatively, or in addition to the multiwavelet reentrant type, cardiac arrhythmias may also have a focal origin, such as when an isolated region of tissue in an atrium fires autonomously in a rapid, repetitive fashion (e.g., another example of the IC ECG data). Ventricular tachycardia (V-tach or VT) is a tachycardia, or fast heart rhythm that originates in one of the ventricles of the heart. This is a potentially life-threatening arrhythmia because it may lead to ventricular fibrillation and sudden death.

For example, aFib occurs when the normal electrical impulses (e.g., another example of the IC ECG data) generated by the sinoatrial node are overwhelmed by disorganized electrical impulses (e.g., signal interference) that originate in the atria veins and PVs causing irregular impulses to be conducted to the ventricles. An irregular heartbeat results, and may last from minutes to weeks, or even years. aFib is often a chronic condition that leads to a small increase in the risk of death often due to strokes. A line of treatment for aFib is medication that either slows the heart rate or revert the heart rhythm back to normal. Additionally, persons with aFib are often given anticoagulants to protect them from the risk of stroke. The use of such anticoagulants comes with its own risk of internal bleeding. In some patients, medication is not sufficient and their aFib is deemed to be drug-refractory, i.e., untreatable with standard pharmacological interventions. Synchronized electrical cardioversion may also be used to convert aFib to a normal heart rhythm. Alternatively, aFib patients are treated by catheter ablation.

A catheter ablation-based treatment may include mapping the electrical properties of heart tissue, especially the endocardium and the heart volume, and selectively ablating cardiac tissue by application of energy. Electrical or cardiac mapping (e.g., implemented by any electrophysiological cardiac mapping system and technique described herein) includes creating a map of electrical potentials (e.g., a voltage map) of the wave propagation along the heart tissue or a map of arrival times (e.g., a LAT map) to various tissue located points. Electrical or cardiac mapping (e.g., a cardiac map) may be used for detecting local heart tissue dysfunction. Ablations, such as those based on cardiac mapping, can cease or modify the propagation of unwanted electrical signals from one portion of the heart 12 to another.

The ablation process damages the unwanted electrical pathways by formation of non-conducting lesions. Various energy delivery modalities have been disclosed for forming lesions, and include use of microwave, laser and more commonly, radiofrequency energies to create conduction blocks along the cardiac tissue wall. Another example of an energy delivery technique includes irreversible electropora-tion (IRE), which provides high electric fields that damage cell membranes. In a two-step procedure (e.g., mapping followed by ablation) electrical activity at points within the heart 12 is typically sensed and measured by advancing the catheter 14 containing one or more electrical sensors (e.g., electrodes 26) into the heart 12 and obtaining/acquiring data at a multiplicity of points (e.g., as biometric data generally, or as ECG data specifically). This ECG data is then utilized to select the endocardial target areas, at which ablation is to be performed.

Cardiac ablation and other cardiac electrophysiological procedures have become increasingly complex as clinicians treat challenging conditions such as atrial fibrillation and ventricular tachycardia. The treatment of complex arrhyth-mias can now rely on the use of 3D mapping systems to reconstruct the anatomy of the heart chamber of interest. In this regard, the generation engine 101 employed by the system 10 herein manipulates and evaluates the biometric data generally, or the ECG data specifically, to produce improved tissue data that enables more accurate diagnosis, images, scans, and/or maps for treating an abnormal heart-beat or arrhythmia. For example, cardiologists rely upon software, such as the Complex Fractionated Atrial Electro-grams (CFAE) module of the CARTO® 3 3D mapping system, produced by Biosense Webster, Inc. (Diamond Bar, Calif.), to generate and analyze ECG data. The generation engine 101 of the system 10 enhances this software to generate and analyze the improved biometric data, which further provide multiple pieces of information regarding electrophysiological properties of the heart 12 (including the scar tissue) that represent cardiac substrates (anatomical and functional) of aFib.

Accordingly, the system 10 can implement a 3D mapping system, such as CARTO® 3 3D mapping system, to localize the potential arrhythmogenic substrate of the cardiomyopa-thy in terms of abnormal ECG detection. The substrate linked to these cardiac conditions is related to the presence of fragmented and prolonged ECGs in the endocardial and/or epicardial layers of the ventricular chambers (right and left). For instance, areas of low or medium voltage may exhibit ECG fragmentation and prolonged activities. Fur-ther, during sinus rhythm, areas of low or medium voltage may corresponds to a critical isthmus identified during sustained and organized ventricular arrhythmias (e.g., applies to non-tolerated ventricular tachycardias, as well as in the atria). In general, abnormal tissue is characterized by low-voltage ECGs. However, initial clinical experience in endo-epicardial mapping indicates that areas of low-voltage are not always present as the sole arrhythmogenic mecha-nism in such patients. In fact, areas of low or medium voltage may exhibit ECG fragmentation and prolonged activities during sinus rhythm, which corresponds to the critical isthmus identified during sustained and organized ventricular arrhythmias, e.g., applies only to non-tolerated ventricular tachycardias. Moreover, in many cases, ECG fragmentation and prolonged activities are observed in the regions showing a normal or near-normal voltage amplitude (>1-1.5 mV). Although the latter areas may be evaluated according to the voltage amplitude, they cannot be consid-ered as normal according to the intracardiac signal, thus representing a true arrhythmogenic substrate. The 3D map-ping may be able to localize the arrhythmogenic substrate on the endocardial and/or epicardial layer of the right/left ventricle, which may vary in distribution according to the extension of the main disease.

As another example operation, cardiac mapping may be implemented by the system 10 using one or more multiple-electrode catheters (e.g., the catheter 14). Multiple-electrode catheters are used to stimulate and map electrical activity in the heart 12 and to ablate sites of aberrant electrical activity. In use, the multiple-electrode catheter is inserted into a major vein or artery, e.g., femoral vein, and then guided into the chamber of the heart 12 of concern. A typical ablation procedure involves the insertion of the catheter 14 having at least one electrode 26 at its distal end, into a heart chamber. A reference electrode is provided, taped to the skin of the patient or by means of a second catheter that is positioned in or near the heart or selected from one or the other electrodes 26 of the catheter 14. Radio frequency (RF) current is applied to a tip electrode 26 of the ablating catheter 14, and current flows through the media that surrounds it (e.g., blood and tissue) toward the reference electrode. The distribution of current depends on the amount of electrode surface in contact with the tissue as compared to blood, which has a higher conductivity than the tissue. Heating of the tissue occurs due to its electrical resistance. The tissue is heated sufficiently to cause cellular destruction in the cardiac tissue resulting in formation of a lesion within the cardiac tissue which is electrically non-conductive. During this process, heating of the tip electrode 26 also occurs as a result of conduction from the heated tissue to the electrode itself. If the electrode temperature becomes sufficiently high, possi-bly above 60 degrees Celsius, a thin transparent coating of dehydrated blood protein can form on the surface of the electrode 26. If the temperature continues to rise, this dehydrated layer can become progressively thicker resulting in blood coagulation on the electrode surface. Because dehydrated biological material has a higher electrical resis-tance than endocardial tissue, impedance to the flow of electrical energy into the tissue also increases. If the imped-ance increases sufficiently, an impedance rise occurs, and the catheter 14 must be removed from the body and the tip electrode 26 cleaned.

Figure 2:
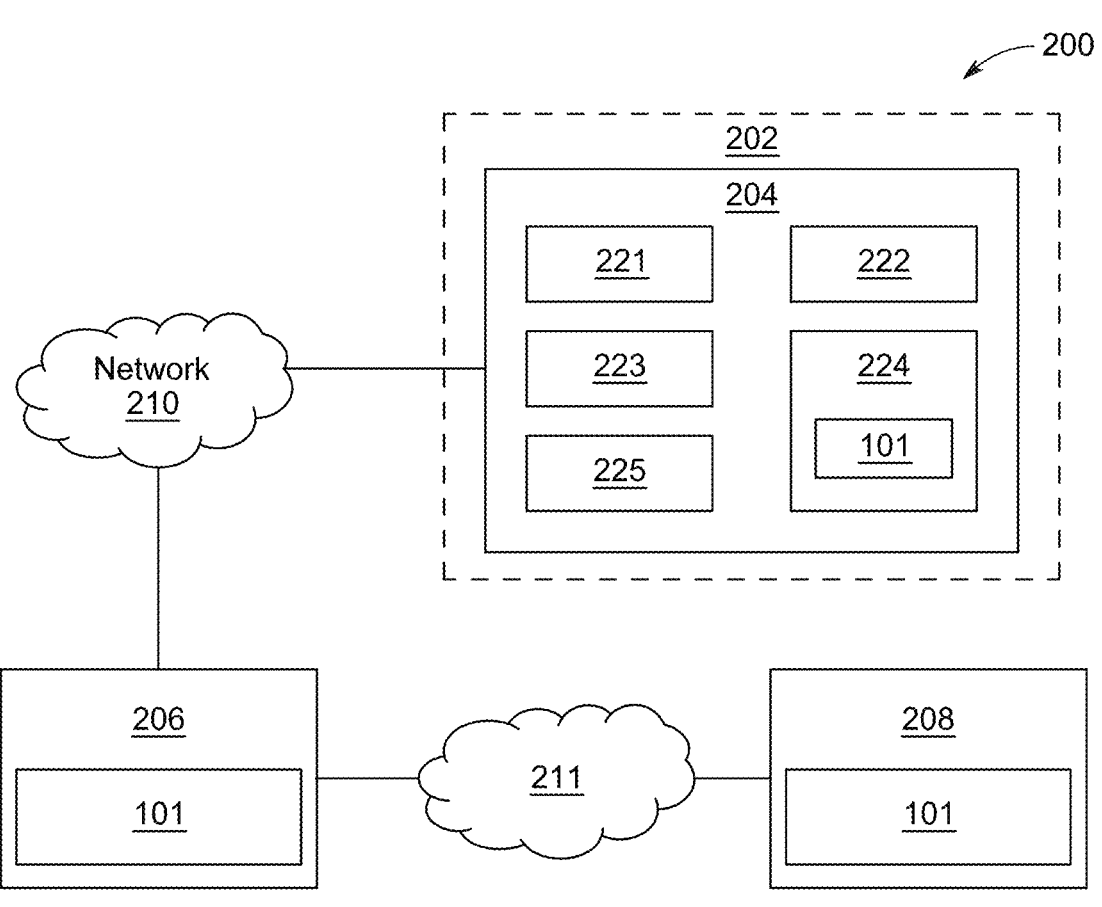
FIG. 2 illustrates a block diagram of an example system for generating a digital twin of atria for aFib patients according to one or more embodiments.

Turning now to FIG. 2, a diagram of a system 200 in which one or more features of the disclosure subject matter can be implemented is illustrated according to one or more embodiments. The system 200 can be configured to generate a digital twin of atria for aFib patients.

The system 200 includes, in relation to a patient 202 (e.g., an example of the patient 23 of FIG. 1), an apparatus 204, a local computing device 206, a remote computing system 208, a first network 210, and a second network 211. Further, the apparatus 204 can include a biometric sensor 221 (e.g., an example of the catheter 14 of FIG. 1), a processor 222, a user input (UI) sensor 223, a memory 224, and a trans-ceiver 225. Note that the generation engine 101 of FIG. 1 is reused in FIG. 2 for ease of explanation and brevity.

According to an embodiment, the apparatus 204 can be an example of the system 10 of FIG. 1, where the apparatus 204 can include both components that are internal to the patient and components that are external to the patient. According to another embodiment, the apparatus 204 can be an appa-ratus that is external to the patient 202 that includes an attachable patch (e.g., that attaches to a patient's skin). According to another embodiment, the apparatus 204 can be internal to a body of the patient 202 (e.g., subcutaneously implantable), where the apparatus 204 can be inserted into the patient 202 via any applicable manner including orally injecting, surgical insertion via a vein or artery, an endoscopic procedure, or a laparoscopic procedure. According to an embodiment, while a single apparatus 204 is shown in FIG. 2, example systems may include a plurality of apparatuses.

Accordingly, the apparatus 204, the local computing device 206, and/or the remote computing system 208 can be programed to execute computer instructions with respect the generation engine 101. As an example, the memory 223 stores these instructions for execution by the processor 222 so that the apparatus 204 can receive and process the biometric data via the biometric sensor 201. In this way, the processor 222 and the memory 223 are representative of processors and memories of the local computing device 206 and/or the remote computing system 208.

The apparatus 204, local computing device 206, and/or the remote computing system 208 can be any combination of software and/or hardware that individually or collectively store, execute, and implement the generation engine 101 and functions thereof. Further, the apparatus 204, local computing device 206, and/or the remote computing system 208 can be an electronic, computer framework comprising and/or employing any number and combination of computing device and networks utilizing various communication technologies, as described herein. The apparatus 204, local computing device 206, and/or the remote computing system 208 can be easily scalable, extensible, and modular, with the ability to change to different services or reconfigure some features independently of others.

The networks 210 and 211 can be a wired network, a wireless network, or include one or more wired and wireless networks. According to an embodiment, the network 210 is an example of a short-range network (e.g., local area network (LAN), or personal area network (PAN)). Information can be sent, via the network 210, between the apparatus 204 and the local computing device 206 using any one of various short-range wireless communication protocols, such as Bluetooth, Wi-Fi, Zigbee, Z-Wave, near field communications (NFC), ultra-band, Zigbee, or infrared (IR). Further, the network 211 is an example of one or more of an Intranet, a local area network (LAN), a wide area network (WAN), a metropolitan area network (MAN), a direct connection or series of connections, a cellular telephone network, or any other network or medium capable of facilitating communication between the local computing device 206 and the remote computing system 208. Information can be sent, via the network 211, using any one of various long-range wireless communication protocols (e.g., TCP/IP, HTTP, 3G, 4G/LTE, or 5G/New Radio). Note that for either network 210 and 211 wired connections can be implemented using Ethernet, Universal Serial Bus (USB), RJ-11 or any other wired connection and wireless connections can be implemented using Wi-Fi, WiMAX, and Bluetooth, infrared, cellular networks, satellite or any other wireless connection methodology.

In operation, the apparatus 204 can continually or periodically obtain, monitor, store, process, and communicate via network 210 the biometric data associated with the patient 202. Further, the apparatus 204, local computing device 206, and/the remote computing system 208 are in communication through the networks 210 and 211 (e.g., the local computing device 206 can be configured as a gateway between the apparatus 204 and the remote computing system 208). For instance, the apparatus 204 can be an example of the system 10 of FIG. 1 configured to communicate with the local computing device 206 via the network 210. The local computing device 206 can be, for example, a stationary/standalone device, a base station, a desktop/laptop computer, a smart phone, a smartwatch, a tablet, or other device configured to communicate with other devices via networks 211 and 210. The remote computing system 208, implemented as a physical server on or connected to the network 211 or as a virtual server in a public cloud computing provider (e.g., Amazon Web Services (AWS)®) of the network 211, can be configured to communicate with the local computing device 206 via the network 211. Thus, the biometric data associated with the patient 202 can be communicated throughout the system 200.

Elements of the apparatus 204 are now described. The biometric sensor 221 may include, for example, one or more transducers configured to convert one or more environmental conditions into an electrical signal, such that different types of biometric data are observed/obtained/acquired. For example, the biometric sensor 221 can include one or more of an electrode (e.g., the electrode 26 of FIG. 1), a temperature sensor (e.g., thermocouple), a blood pressure sensor, a blood glucose sensor, a blood oxygen sensor, a pH sensor, an accelerometer, and a microphone.

The processor 222, in executing the generation engine 101, can be configured to receive, process, and manage the biometric data acquired by the biometric sensor 221, and communicate the biometric data to the memory 224 for storage and/or across the network 210 via the transceiver 225. Biometric data from one or more other apparatuses 204 can also be received by the processor 222 through the transceiver 225. Also, as described in more detail herein, the processor 222 may be configured to respond selectively to different tapping patterns (e.g., a single tap or a double tap) received from the UI sensor 223, such that different tasks of a patch (e.g., acquisition, storing, or transmission of data) can be activated based on the detected pattern. In some embodiments, the processor 222 can generate audible feedback with respect to detecting a gesture.

According to one or more embodiments, the generation engine 101 upon execution can receive inputs including images and conduction velocity vector estimations, generate a digital twin of an anatomical structure utilizing the images and the conduction velocity vector estimations, and presenting, via a user interface, the digital twin to provide precision ablation guidance and electrophysiology information of the anatomical structure.

According to one or more embodiments, the generation engine 101 upon execution can perform re-estimation LAT activities based on the digital twin after performing one or more ablation (note that the ablation can be electroporation). In this case, the digital twin enables the generation engine 101 to generate a LAT map based on identifying a heartbeat source (e.g., a sinoatrial or SA node) and to calculate signal progress in the heart 12 based on the CV for each direction. One or more of the technical effects, advantages, and benefits of the generation engine 101, thus, include enabling a real LAT map (as generated to day in CARTO® 3) and a digital twin LAT map to be provided on the same interface. Further, after ablating, using ablation estimation models (such as CARTO VISITAG™ model), the CV of the ablated location can be updated by the generation engine 101. Accordingly, the digital twin LAT map can also be updated based on 1250f the CV updates. One or more of the technical effects, advantages, and benefits of the generation engine 101, thus, include enabling a simulation of the LAT map after ablation without remapping the heart 14. Thus, according to one or more embodiments, the generation engine 101 can generate the digital twin LAT map based on the digital twin model, and can update CV vector estimations of ablated cells/tissue in the digital twin model based on an ablation model that influenced the digital twin LAT map. 1250

The UI sensor 223 includes, for example, a piezoelectric sensor or a capacitive sensor configured to receive a user input, such as a tapping or touching. For example, the UI sensor 223 can be controlled to implement a capacitive coupling, in response to tapping or touching a surface of the apparatus 204 by the patient 202. Gesture recognition may be implemented via any one of various capacitive types, such as resistive capacitive, surface capacitive, projected capacitive, surface acoustic wave, piezoelectric and infra-red touching. Capacitive sensors may be disposed at a small area or over a length of the surface, such that the tapping or touching of the surface activates the monitoring device.

The memory 224 is any non-transitory tangible media, such as magnetic, optical, or electronic memory (e.g., any suitable volatile and/or non-volatile memory, such as ran-dom-access memory or a hard disk drive). The memory 224 stores the computer instructions for execution by the pro-cessor 222.

The transceiver 225 may include a separate transmitter and a separate receiver. Alternatively, the transceiver 225 may include a transmitter and receiver integrated into a single device.

In operation, the apparatus 204, utilizing the generation engine 101, observes/obtains the biometric data of the patient 202 via the biometric sensor 221, stores the biometric data in the memory, and shares this biometric data across the system 200 via the transceiver 225. The generation engine 101 can then utilize models, far field reduction algorithms, neural networks, ML, and/or AI to perform signal processing operations that generate a digital twin of atria for atrial fibrillation (aFib) patients.

Figure 3:
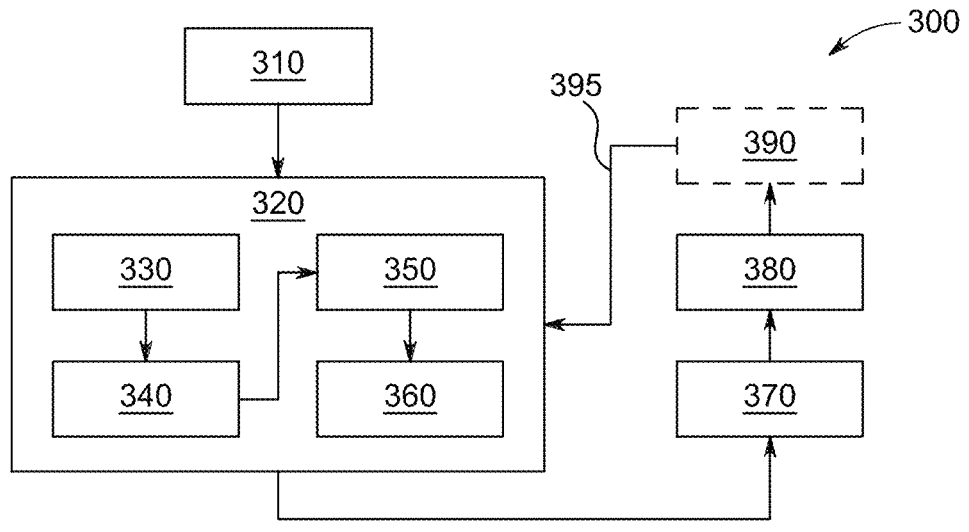
FIG. 3 illustrates a method according to one or more embodiments.

Turning now to FIG. 3, a method 300 (e.g., performed by the generation engine 101 of FIG. 1 and/or of FIG. 2) is illustrated according to one or more embodiments. The method 300 can be an example of an ablation procedure guidance method for navigating atria of a heart. The method 300 addresses a need for improved ablation location deter-mining techniques by providing a multi-step manipulation of electrical activity of the heart 12 (e.g., accounts for arrhythmia triggers, as well as information regarding atrial wall substances) that enables an improved understanding an electrophysiology with more precision via the digital twin.

The method begins at block 310, where the generation engine 101 receives one or more inputs. The one or more inputs can include biometric data, as described herein, as well as one or more images (e.g., CTs, MRIs, etc.) of the heart 12. The one or more inputs can be real-time data and patient specific. More particularly, the one or more inputs can include baseline recordings of IC ECG and/or BS ECG, previous/current CV vector estimations, and/or a lattice Boltzmann model for simulating typical waves propagating along the atria. According to one or more embodiments, the system 10 can utilize a multielectrode catheter (e.g., the catheter 14) to obtain multiple acquisitions (e.g., the base-line recordings) from a cardiac region covered by the electrodes. According to one or more embodiments, the inputs include images, conduction velocity vector estima-tions, and baseline recordings or a lattice Boltzmann model. Further, the inputs can be arrhythmogenic activity from IC ECG and/or BS ECG.

At block 320, the generation engine 101 generates a digital twin. For example, the generation engine 101 creates a digital twin of a left atria of the heart 12 for the aFib patient 23. The digital twin of the heart 12 can be based on the images and other inputs. According to one or more embodiments, the generation engine 101 generates the digital twin of the heart 12 utilizing the images and the conduction velocity vector estimations. The digital twin can also be based on the baseline recordings, the CV vector estimations, and/or the lattice Boltzmann model. Thus, once the genera-tion engine 101 has the images and other inputs, the gen-eration engine 101 can construct the anatomy to determine how the electricity flows through that anatomy. One or more operations of generating the digital twin at block 320 can include, but are not limited to, performing a direction of arrival (DOA) estimation (330), clustering (340), voxelizing (350), and dynamic 3D generation (360). In this regard, the generation engine 1010 determines electricity flows through the heart 12 based on performing one or more of DOA estimations, clustering, voxelizing, and dynamic three-di-mensional generation. While the operations of generating the digital twin are described further herein, a brief expla-nation of each is provided for ease of understanding.

At blocks 330 and 340, the DOA estimation and clustering can be a bottom-up approach to estimate local CV vectors by performing a segment-by-segment analysis of atrial activa-tion from unipolar signals. Note that DOA estimations automatically identify CV vectors of arrhythmogenic activ-ity (e.g., the system 10 can utilize DOA estimations to automatically identify the CV vectors estimations and to generate the digital twin). That is, once all segments are processed, the generation engine 101 clusters to detect DOA clusters (e.g., an output of the clustering can be 1-3 typical conduction velocity vectors). More particularly, the bottom-up stage approach outputs conduction velocity vectors and focal source location per points of electrophysiology mea-surements, with a last stage using Lattice Boltzmann Model for estimating patterns of electrical flows simulations based on focal source.

At block 350, the generation engine 101 voxelizes (i.e., processes one or more voxels) to find a best CV vector. In this regard, the atria are voxelated into K voxels (i.e., the atria is divided into one or more voxels), and each voxel sees only its six immediate nearest neighbors. Further, the gen-eration engine 101 uses a probability for seeing an activation wave in an immediate neighbor to determine the best CV vector. At block 360, the generation engine 101 executes a dynamic 3D generation that presents a wave (along the best CV vector). In this regard, the digital twin that is built from the one or more inputs (e.g., the constructed anatomy from the images) is aligned with the dynamic 3D generation.

At block 370, the generation engine 101 presents the digital twin in a user interface for the physician 24. Accord-ing to one or more embodiments, the generation engine 101 presents the digital twin to provide precision ablation guid-ance and provide electrophysiology information of the ana-tomical structure (i.e., the heart 12). For instance, the precision ablation guidance of the user interface can include one or more simulations showing how electricity flows through the digital twin based the conduction velocity vector estimations (e.g., based on the best CV vector) and/or one or more interactions between focal activities with respect to the digital twin and determining a foci for ablation based on the one or more interactions. More particularly, the generation engine 101 acts a guiding tool for an ablation procedure before any ablation is performed. In this way, the physician 24 can evaluate a real-time condition of the atria of the heart 12 and interact with the digital twin accordingly.

At block 380, the generation engine 101 receives one or more additional inputs. The one or more additional inputs can be real-time data and patient specific. The one or more inputs can include biometric data, catheter movements, CT images, MRI images, real time ultrasound images, additional IC ECG and/or BS ECG recordings, and/or updated CV vector estimations. According to one or more embodiments, the generation engine 101 receives the one or more additional inputs and generates one or more different ablation approach suggestions for an ablation procedure, as well as performs a remapping operation of the digital twin (based on the one or more additional inputs). For example, the physician 24 makes one or more decisions after viewing the digital twin presented at block 370, such as moving the catheter 14 to a new position. The generation engine 101 utilizes the new position and updated biometric information associated with the new position (as the one or more additional inputs) to generate simulations. The generation engine 101 simulates different ablation approaches and suggests one that reduces the arrhythmia with minimum area of ablation. The generation engine 101 simulates interaction between focal activities to determine which of the focal are more important for ablation. The technical effects and benefits of the method 300 include enabling the generation engine 101 to include actual scars using bipolar voltage map or simulated scars based on the assumption that the physician 24 is going to ablate in each location. According to one or more embodiments, the operations of block 380 can be optional.

At dashed-block 380 (optional), ablation occurs. This optional step can be performed by the physician 24, based on the simulations presented at block 370 and 380 in accordance with the one or more additional inputs. After the one or more additional inputs are received and/or the ablation is performed, the generation engine 101 can perform a remapping operation (represented by arrow 395) by returning to block 320.

Figure 4:
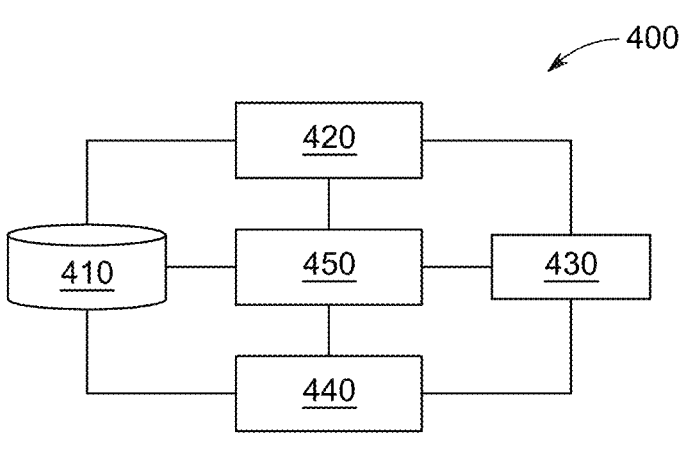
FIG. 4 illustrates a graphical depiction of an artificial intelligence system according to one or more embodiments.
Figure 5:
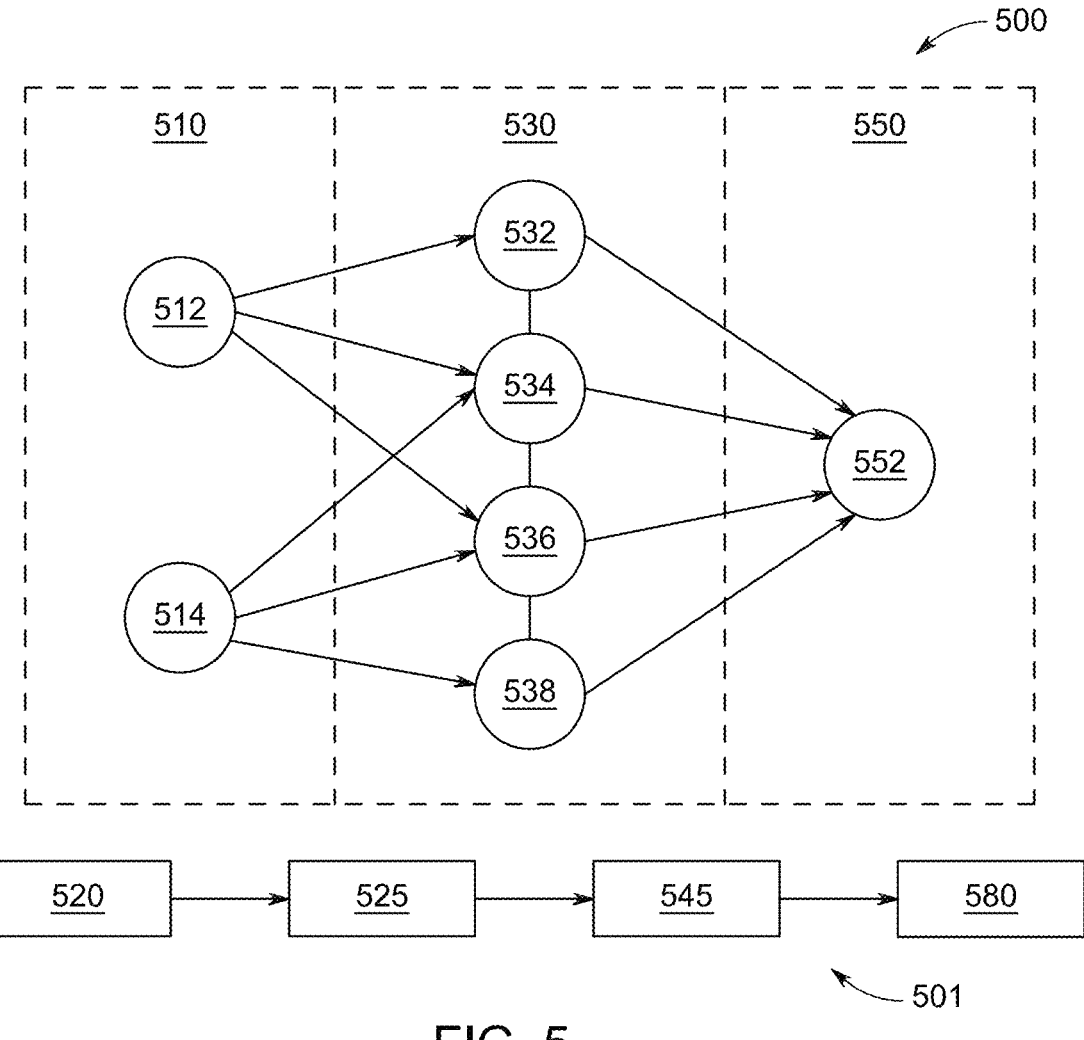
FIG. 5 illustrates an example of a neural network and a block diagram of a method performed in the neural network according to one or more embodiments.

All or part of the method 300 can be implemented by the generation engine 101 with respect to ML/AI as described herein. FIG. 4 illustrates a graphical depiction of an AI system 400 according to one or more embodiments. As shown, the AI system 400 includes data 410 (e.g., biometric data) that can be stored on a memory or other storage unit. Further, the AI system 400 includes a machine 420 and a model 430, which represent software aspects of the generation engine 101 of FIGS. 1-2 (e.g., ML/AI algorithm therein), The machine 420 and the model 430 together can generate an outcome 440. The AI system 400 can include hardware 450, which can represent the catheter 14 of FIG. 1, the workstation 55 of FIG. 1, and/or the apparatus 204 of FIG. 2. The description of FIGS. 4-5 is made with reference to FIGS. 1-3 for ease of understanding where appropriate. In general, the ML/AI algorithms of the AI system 400 (e.g., as implemented by the generation engine 101 of FIGS. 1-2) operate with respect to the hardware 450, using the data 410, to train the machine 420, build the model 430, and predict the outcomes 440.

For instance, the machine 420 operates as software controller executing on the hardware 450. The data 410 (e.g., the biometric data as described herein) can be on-going data (i.e., data that is being continuously collected) or output data associated with the hardware 450. The data 410 can also include currently collected data (e.g., position of the catheter 14), historical data, or other data from the hardware 450; can include measurements during a surgical procedure and may be associated with an outcome of the surgical procedure; can include a temperature of the heart 12 of FIG. 1 collected and correlated with an outcome of a heart procedure (or one or more of LATs, electrical activity, topology, bipolar mapping, reference activity, ventricle activity, dominant frequency, impedance); and can be related to the hardware 450. The data 410 can be divided by the machine 420 into one or more subsets.

Further, the machine 420 trains, which can include an analysis and correlation of the data 410 collected. For example, in the case of the heart, the data 410 of temperature and outcome may be trained to determine if a correlation or link exists between the temperature of the heart 12 of FIG. 1 during the heart procedure and the positive or negative procedure outcome. In accordance with another embodiment, training the machine 420 can include self-training by the generation engine 101 of FIG. 1 utilizing the one or more subsets. In this regard, for example, the generation engine 101 of FIG. 1 learns to generate digital twins and simulate wave propagations.

Moreover, the model 430 is built on the data 410. Building the model 430 can include physical hardware or software modeling, algorithmic modeling, and/or the like that seeks to represent the data 410 (or subsets thereof) that has been collected and trained. In some aspects, building of the model 430 is part of self-training operations by the machine 420. The model 430 can be configured to model the operation of hardware 450 and model the data 410 collected from the hardware 450 to predict the outcome 440 achieved by the hardware 450. Predicting the outcomes 440 (of the model 430 associated with the hardware 450) can utilize a trained model 430. For example and to increase understanding of the disclosure, in the case of the heart, if the temperature during the procedure that is between 36.5 degrees Celsius and 37.89 degrees Celsius (i.e., 97.7 degrees Fahrenheit and 100.2 degrees Fahrenheit) produces more positive results from the heart procedure, the outcome 440 may be predicted in a given procedure using these temperatures. Thus, using the outcome 440 that is predicted, the machine 420, the model 430, and the hardware 450 can be configured accordingly.

Thus, for the AI system 400 to operate as described, the ML/AI algorithms therein can include neural networks. In general, a neural network is a network or circuit of neurons, or in a modern sense, an artificial neural network (ANN), composed of artificial neurons or nodes or cells.

For example, an ANN involves a network of processing elements (artificial neurons) which can exhibit complex global behavior, determined by the connections between the processing elements and element parameters. These connections of the network or circuit of neurons are modeled as weights. A positive weight reflects an excitatory connection, while negative values mean inhibitory connections. Inputs are modified by a weight and summed using a linear combination. An activation function may control the amplitude of the output. For example, an acceptable range of output is usually between 0 and 1, or it could be −1 and 1. In most cases, the ANN is an adaptive system that changes its structure based on external or internal information that flows through the network.

In more practical terms, neural networks are non-linear statistical data modeling or decision-making tools that can be used to model complex relationships between inputs and outputs or to find patterns in data. Thus, ANNs may be used for predictive modeling and adaptive control applications, while being trained via a dataset. Note that self-learning resulting from experience can occur within ANNs, which can derive conclusions from a complex and seemingly unrelated set of information. The utility of artificial neural network models lies in the fact that they can be used to infer a function from observations and also to use it. Unsupervised neural networks can also be used to learn representations of the input that capture the salient characteristics of the input distribution, and more recently, deep learning algorithms, which can implicitly learn the distribution function of the observed data. Learning in neural networks is particularly useful in applications where the complexity of the data (e.g., the biometric data) or task (e.g., monitoring, diagnosing, and treating any number of various diseases) makes the design of such functions by hand impractical.

For the AI system 400, the ML/AI algorithms therein can include neural networks that are divided generally according to tasks to which they are applied. These divisions tend to fall within the following categories: regression analysis (e.g., function approximation) including time series prediction and modeling; classification including pattern and sequence recognition; novelty detection and sequential decision making; data processing including filtering; clustering; blind signal separation, and compression. For example, application areas of ANNs include medical diagnosis and treatment to assist with creating a semantic profile of patient biometric data emerging from medical procedures.

According to one or more embodiments, the neural network can implement a long short-term memory neural network architecture, a convolutional neural network (CNN) architecture, or other the like. The neural network can be configurable with respect to a number of layers, a number of connections (e.g., encoder/decoder connections), a regularization technique (e.g., dropout); and an optimization feature.

The long short-term memory neural network architecture includes feedback connections and can process single data points (e.g., such as images), along with entire sequences of data (e.g., such as speech or video). A unit of the long short-term memory neural network architecture can be composed of a cell, an input gate, an output gate, and a forget gate, where the cell remembers values over arbitrary time intervals and the gates regulate a flow of information into and out of the cell.

The CNN architecture is a shared-weight architecture with translation invariance characteristics where each neuron in one layer is connected to all neurons in the next layer. The regularization technique of the CNN architecture can take advantage of the hierarchical pattern in data and assemble more complex patterns using smaller and simpler patterns. If the neural network implements the CNN architecture, other configurable aspects of the architecture can include a number of filters at each stage, kernel size, a number of kernels per layer.

Turning now to FIG. 5, an example of a neural network 500 and a block diagram of a method 501 performed in the neural network 500 are shown according to one or more embodiments. The neural network 500 operates to support implementation of the ML/AI algorithms (e.g., as implemented by the generation engine 101 of FIGS. 1-2) described herein. The neural network 500 can be implemented in hardware, such as the machine 420 and/or the hardware 450 of FIG. 4. As indicated herein, the description of FIGS. 4-5 is made with reference to FIGS. 1-3 for ease of understanding where appropriate.

In an example operation, the generation engine 101 of FIG. 1 includes collecting the data 410 from the hardware 450. In the neural network 500, an input layer 510 is represented by a plurality of inputs (e.g., inputs 512 and 514 of FIG. 5). With respect to block 520 of the method 501, the input layer 510 receives the inputs 512 and 514. The inputs 512 and 514 can include biometric data. For example, the collecting of the data 410 can be an aggregation of biometric data (e.g., BS ECG data, IC ECG data, and ablation data, along with catheter electrode position data), from one or more procedure recordings of the hardware 450 into a dataset (as represented by the data 410).

At block 525 of the method 501, the neural network 500 encodes the inputs 512 and 514 utilizing any portion of the data 410 (e.g., the dataset and predictions produced by the AI system 400) to produce a latent representation or data coding. The latent representation includes one or more intermediary data representations derived from the plurality of inputs. According to one or more embodiments, the latent representation is generated by an element-wise activation function (e.g., a sigmoid function or a rectified linear unit) of the generation engine 101 of FIG. 1. As shown in FIG. 5, the inputs 512 and 514 are provided to a hidden layer 530 depicted as including nodes 532, 534, 536, and 538. The neural network 500 performs the processing via the hidden layer 530 of the nodes 532, 534, 536, and 538 to exhibit complex global behavior, determined by the connections between the processing elements and element parameters. Thus, the transition between layers 510 and 530 can be considered an encoder stage that takes the inputs 512 and 514 and transfers it to a deep neural network (within layer 530) to learn some smaller representation of the input (e.g., a resulting the latent representation).

The deep neural network can be a CNN, a long short-term memory neural network, a fully connected neural network, or combination thereof. The inputs 512 and 514 can be intracardiac ECG, body surface ECG, or intracardiac ECG and body surface ECG. This encoding provides a dimensionality reduction of the inputs 512 and 514. Dimensionality reduction is a process of reducing the number of random variables (of the inputs 512 and 514) under consideration by obtaining a set of principal variables. For instance, dimensionality reduction can be a feature extraction that transforms data (e.g., the inputs 512 and 514) from a high-dimensional space (e.g., more than 10 dimensions) to a lower-dimensional space (e.g., 2-3 dimensions). The technical effects and benefits of dimensionality reduction include reducing time and storage space requirements for the data 410, improving visualization of the data 410, and improving parameter interpretation for ML. This data transformation can be linear or nonlinear. The operations of receiving (block 520) and encoding (block 525) can be considered a data preparation portion of the multi-step data manipulation by the generation engine 101.

At block 545 of the method 510, the neural network 500 decodes the latent representation. The decoding stage takes the encoder output (e.g., the resulting the latent representation) and attempts to reconstruct some form of the inputs 512 and 514 using another deep neural network. In this regard, the nodes 532, 534, 536, and 538 are combined to produce in the output layer 550 an output 552, as shown in block 560 of the method 510. That is, the output layer 590 reconstructs the inputs 512 and 514 on a reduced dimension but without the signal interferences, signal artifacts, and signal noise. Examples of the output 552 include cleaned biometric data (e.g., clean/denoised version of IC ECG data or the like). The technical effects and benefits of the cleaned biometric data include enabling more accurate monitor, diagnosis, and treatment any number of various diseases.

According to one or more embodiments, the generation engine 101 is described with respect to creating a digital twin of an atria of the heart 12 (e.g., Atria Digital Twin or ADT) for an aFib patient (e.g., the patient 120). As noted herein, aFib is a major global healthcare challenge. For example, aFib initiation and maintenance are incompletely understood, which has hindered the development of effective and reliable therapy. Treatment for aFib is often through catheter ablation, where the regions of myocardium determined to be responsible for initiating or perpetuating the disturbance are targeted and made electrically inactive through the localized application of radio-frequency energy or freezing.

For instance, for paroxysmal aFib, catheter ablation delivers relatively good outcomes, with success rates in a region of 80% to 90%. However, catheter ablation therapy for persistent aFib patients is less effective with success rates of approximately 50% despite all forms of adjunctive ablation strategies (also, approximately 33% of ablation procedures are performed in patients with persistent or long-standing persistent aFib). Pulmonary vein isolation (PVI) can be a first approach, but other ablation strategies are being developed to increase the effectiveness of the treatment for this segment of patients.

There are number of driving mechanisms responsible for aFib maintenance. Foci, rotors, and epi-endo disassociation. Recent clinical studies have targeted the foci, complex fractionated atrial electrograms (CFAE), and high dominant frequency (DF). However, none of these ablation strategies have been shown to add any value to the PVI approach. One or more reasons that these ablation strategies do not add value may include that these ablation strategies investigated only one modality in persistent aFib and connected that modality (e.g., simple or complex, focal behavior or non-focal behavior, early or late, fractionated or non-fractionated) to success or failure to obtain freedom from aFib after year or more from the ablation procedure, while much of the EP and ablation parameters being ignored.

The generation engine 101 overcomes these concerns by generating and providing an ADT for aFib patients (e.g., the patient 120). For example, the ADT models IC ECG data during baseline recordings of ablation procedure and creates match (e.g., like-for-like) of all available clinical observations. Base on the ADT, the generation engine 101 can test different ablation approaches and predict corresponding successes for acute and long-term termination of aFib. Accordingly, one or more advantages, technical effects, and/or benefits of the generation engine 101 includes a cost effective, safe, and ethical solution for ablation therapy investigation. That is, the generation engine 101 creates a patient specific model of an atrium (i.e., ADT). The patient specific model can address a number of challenges with respect to 3D representations, electrophysiology modeling, and other modeling of the atria. The generation engine 101 can, also, simulate a time varying contraction and conduction flow, simulate a hemodynamics flow of the atria, and apply the same when create digital twins of ventricles. The generation engine 101, also, overcomes these concerns by using IC ECG, 3D imaging of the atria to estimate CV vectors, and a Lattice Boltzmann model for simulating N typical electrical flows that best fit the data. For example, the generation engine 101 can utilize and apply a deep learning algorithm to estimate the CV vectors per voxel from as set of 12 lead ECG signals. As noted herein with respect to FIG. 5, the generation engine 101 can include a ML/AI architecture for CV estimation from 3D anatomy, BC ECG, and 3D position of the BS electrodes.

According to one or more embodiments, the generation engine 101 generates, as the ADT, a digital twin of a left atria for aFib patients (e.g., the patient 120). This ADT is generated from baseline recordings of IC-ECG, CV vector estimation, and lattice Boltzmann model for simulating typical waves propagating along the left atria, as described herein (see at least FIG. 3). The ADT can include actual scars using a bipolar voltage map or simulated scars based on the assumption that the physician 24 is going to ablate in each location. Therefore, the ADT can be used a guiding tool for ablation procedure. The ADT can, also, simulate different ablation approaches (across the ADT) and select one that reduces the arrhythmia with minimum area of ablation (e.g., an approach that has a smallest effective area). The ADT can simulate one or more interactions between focal activities (with respect to the atrial digital twin) to determine which of the focal are more important for ablation. Note that, given the nature of aFib, the ADT does not assume that an arrythmia repeats itself, such as in digital simulations based on anatomical information and assume a standard electrical conduction Turning now to FIG. 6, a method 600 is illustrated according to one or more embodiments. Note that block 605 is dotted, indicating an input block; blocks 610, 615, 620, 625, 630, 635, 640, 645, 650, 675, and 680 are dashed, indicating processing blocks; and blocks 655, 665, 670, and 685 are dashed, indicating output blocks. The method 600 conducts velocity estimation and focal source detection based on DOA estimation (i.e., a process for CV and focal detection based on DOA estimation). Note that DOA can be considered a method for automatically identifying CV vectors of arrhythmogenic activity. Further, the method 600 can be a bottom-up approach to estimate local CV vectors, such as by using a multielectrode catheter to obtain multiple acquisitions from a cardiac region covered by the electrodes.

At block 605, the generation engine 101 receives input recordings (e.g., multiple acquisitions from a cardiac region covered by the electrodes). At block 610, the generation engine 101 performs an atrial detection per unipolar signal. At decision block 615. the generation engine 101 performs a segment-by-segment analysis of atrial activation from the unipolar signals.

In parallel, at block 620, the generation engine 101 further projects the catheter 14 into a 2D space. At determination block 625, determines if there is a valid projection, such as the ratio of the sum of two dominant eigenvalues to the sum of three eigenvalues being higher than 95%. That is, if the generation engine 101 is not able to project into the 2D space, the method proceeds to block 630 (as shown by the NO arrow). Otherwise, the method 600 proceeds to block 635 (as shown by the YES arrow). At blocks 630 and 635, a 3D or 2D weighted DOA model estimation is initiated based on the ability to project the catheter into a 2D space.

At decision block 640, the generation engine 101 determines whether the estimation error of the model (e.g., ADT) is high or low. If the estimation error of the model is too high (e.g., greater than 7 milliseconds or msec), then the method 600 proceeds to block 645 (as shown by the NO arrow). At block 645, an iterative mode for DOA estimation is applied. Iterative mode for DOA estimation is illustrated with respect to FIGS. 11-14.

At decision block 650, the generation engine 101 again determines whether the estimation error of the model (e.g., ADT) is high or low (e.g., greater than 7 msec). If the estimation error of the model is too high (e.g., greater than 7 msec), then the method 600 proceeds to output block 655 (as shown by the NO arrow). At output block 655, the generation engine 101 stores any bad segments for/from the DOA.

If a valid DOA is detected at block 640 and or 650 (as shown by the YES arrow), the LAT are corrected at output block 665. At output block 670, one or more DOA points are also stored in the memory 62 until all segments are processed. For instance, the method 600 can loop into decision block 615, such as to finish all segments.

At block 675, once all segments are processed (see Arrow 676), a k-means clustering is performed for the detection of DOA clusters. The k-means clustering can give/provide/generate typical CV vectors per location of the catheter 14 (e.g., a PentaRay® catheter). At block 680, the generation engine 101 executes a detection stage where a focal source detection is initiated (i.e., if an origin of one or more of dominant CV vectors falls within 8 mm from a center of the catheter 14, then a mechanism of focal validation is applied). At output block 685, the generation engine 101 can validate focal sources (e.g., if there are 10 or more earliest S-wave patterns in electrodes in its vicinity).

Figure 6:
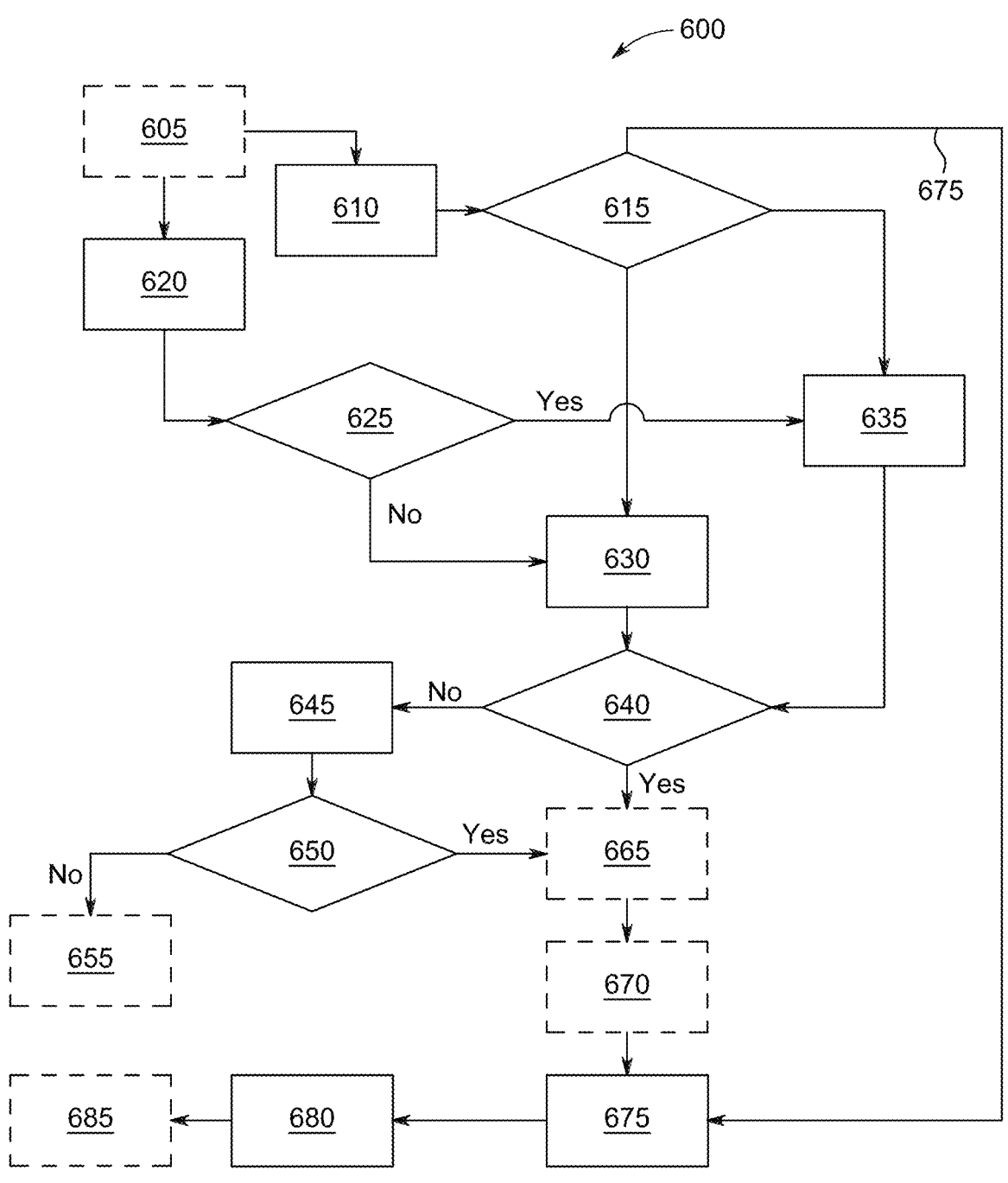
FIG. 6 illustrates a method according to one or more embodiments.

According to one or more embodiments, DOA estimation, foci detection, and LAT improvements, as well as other aspect of FIG. 6, are further described herein.

Regarding a per segment DOA, a model base DOA can be applied for each segment of data. For instance, the model base DOA can include a set of at least 10 local atrial activation with t; being a time of local atrial activity of the i electrode, $i=1, \ldots, m$ $10 \leq m \leq N$, where N is a number of valid electrodes in the catheter 14 (e.g., N=20 for PentaRay® catheter). If the generation engine 101 assumes/determines that a single wave is originated from any point in 3D space and that the single wave travels toward the catheter 14 with a constant CV, then the generation engine 101 can define the $J(\theta)$ the "total cost" of the model according to Equation 1, where $x_i$, $y_i$, $z_i$ are the coordinates of the location of the electrodes and $x_0$, $y_0$, $z_0$ are the coordinates of the location where the DOA is calculated.

$$J(\theta) = \qquad \text{EQUATION 1}$$
$$\frac{1}{m}\sum_{i=m}^{m}\left(v\sqrt{(x_i - x_0)^2 + (y_i - y_0)^2 + (z_i - z_0)^2} + t_0 - t_i\right)^2 +$$
$$\frac{\lambda}{2m}\left(x_0^2 + y_0^2 + z_0^2 + \frac{1}{v^2}\right)$$

That is, the generation engine further defines $d_i=101$ $\sqrt{(x_i-x_0)^2+(y_i-y_0)^2+(z_i-z_0)^2}$ as the distance from a DOA point located at $(x_0, y_0, z_0)$ and arriving at $t_i$ to the i electrode located at $(x_i, y_i, z_i)$. The generation engine 101 further defines $t_0$ as the bias time of arrival for all electrodes and v is 1/CV of the wave. The term $$\frac{\lambda}{2m}\left(x_0^2 + y_0^2 + z_0^2 + \frac{1}{v^2}\right)$$

in $J(\theta)$ is a regularization term that is prefers solutions that are closer to an origin of the catheter 14 and increases a probability to find solutions within the anatomy of the atria. A purpose of the model base DOA is to minimize the total cost $J(\theta)$ by finding the "best" $\theta=(x_0, y_0, z_0, t_0, v)$, that minimizes the total cost $J(\theta)$. The generation engine 101 achieve this purpose by using a gradient descent estimation procedure with a constraint that v is greater than 0. Gradient descent can be based on the observation that if the multivariable function $J(\theta_1)$ at the k'th iteration is defined and differentiable in a neighborhood of a point $\theta_1$, then $J(\theta_1)$ decreases fastest from $\theta_k$ in the direction of the negative gradient of $J(\theta_k)$ according to Equation 2.

$$\theta_{k+1}=\theta_k-\gamma\cdot\nabla J(\theta_1) \qquad \text{EQUATION 2}$$

Not that $\nabla$ represents a differential operation, and $\gamma$ is the learning rate factor. $\gamma$ can be small to ensure conversion and not too small to overcome slow conversion or convergence to a local minimum of $J(\theta)$. According to one or more embodiments, a formal description of gradient descent algorithm can include deriving a differential equation of $J(\theta)$ with respect to each one of the parameters $(x_0, y_0, z_0, t_0, v)$ hence, as shown below by Equations 3-7, respectively.

$$\frac{\partial J(\theta)}{\partial x_0} = -\frac{2}{m}\sum_{i=m}^{m}\frac{(v\cdot d_i + t_0 - t_i)}{d_i}(x_i - x_0) + \frac{\lambda\cdot x_0}{m} \qquad \text{EQUATION 3}$$

$$\frac{\partial J(\theta)}{\partial y_0} = -\frac{2}{m}\sum_{i=m}^{m}\frac{(v\cdot d_i + t_0 - t_i)}{d_i}(y_i - y_0) + \frac{\lambda\cdot y_0}{m} \qquad \text{EQUATION 4}$$

$$\frac{\partial J(\theta)}{\partial z_0} = -\frac{2}{m}\sum_{i=m}^{m}\frac{(v\cdot d_i + t_0 - t_i)}{d_i}(z_i - z_0) + \frac{\lambda\cdot z_0}{m} \qquad \text{EQUATION 5}$$

$$\frac{\partial J(\theta)}{\partial v} = \frac{2}{m}\sum_{i=m}^{m}(v\cdot d_i + t_0 - t_i)\cdot d_i + \frac{\lambda}{m\cdot v^3} \qquad \text{EQUATION 6}$$

$$\frac{\partial J(\theta)}{\partial t_0} = \frac{2}{m}\sum_{i=m}^{m}(v\cdot d_i + t_0 - t_i) \qquad \text{EQUATION 7}$$

Figure 7:
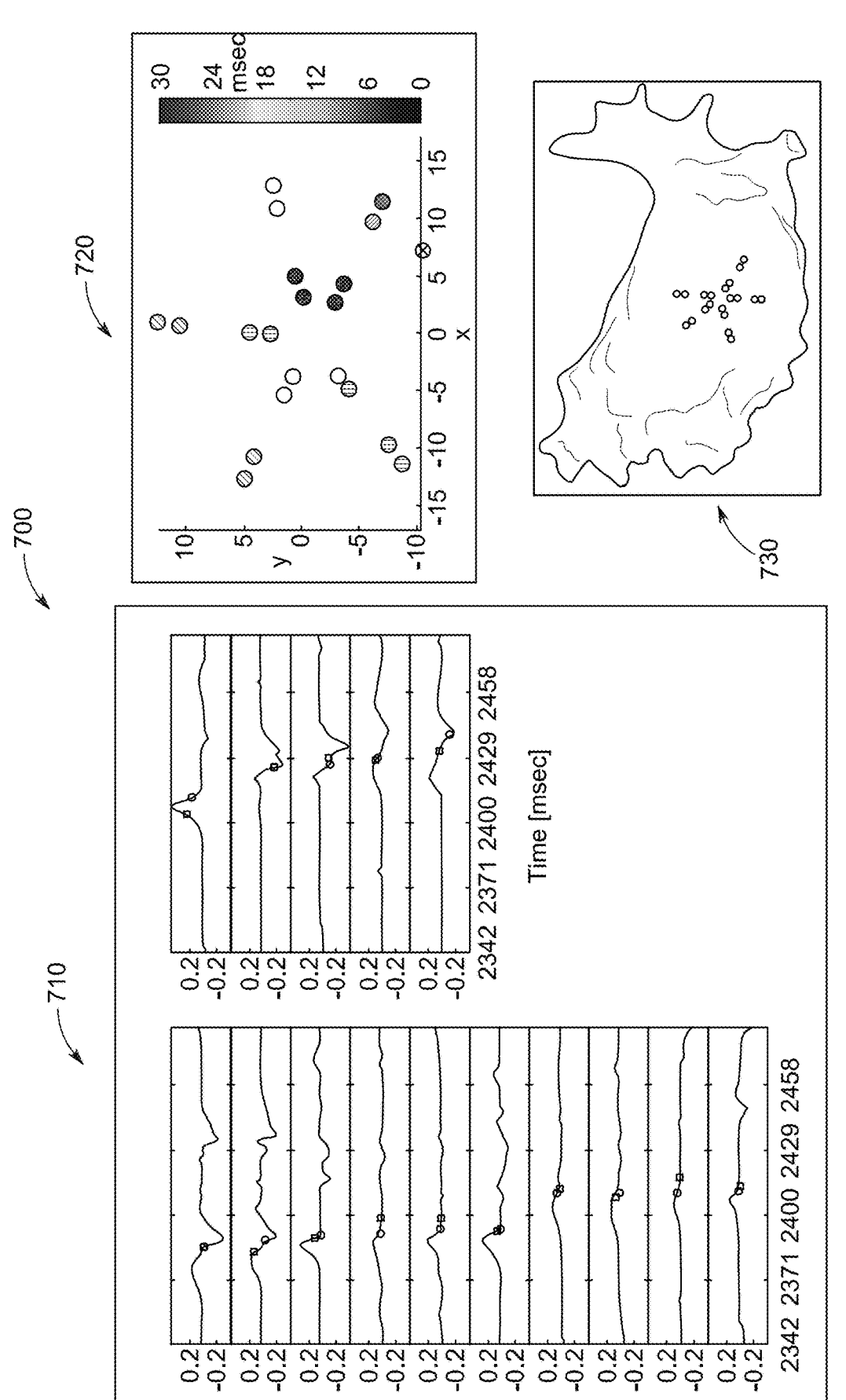
FIG. 7 illustrates an interface according to one or more embodiments.

FIGS. 7-11 illustrate interfaces 700, 800, 900, 1000, and 1100 according to one or more embodiments. The interfaces 700, 800, 900, 1000, and 1100 can be generated by the generation engine 101. The interface 700 of FIG. 7 shows an example of DOA estimation based on a segment of atrial activity. First portion 710 of the interface 700 provides a set of unipolar signals with location of local activation time ($t_i$—circles) and their corresponding estimated-local activation time based on DOA model (squares). An upper FIG. 720 of the interface 700 depicts the estimated focal activity (circle with x inside). The other circles represent location of electrodes in X-Y space. An lower FIG. 730 of the interface 700 represents the actual location of the catheter 14 on the anatomy of the left atria.

Figure 8:
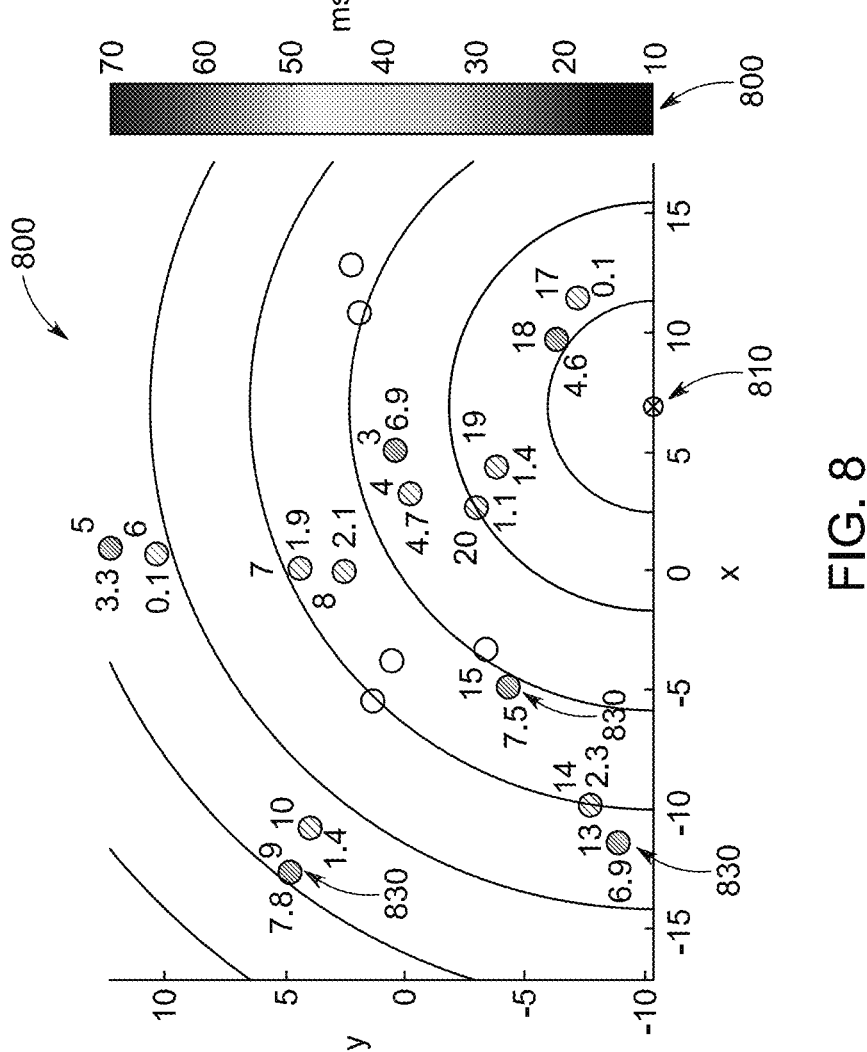
FIG. 8 illustrates an interface according to one or more embodiments.

The interface 800 of FIG. 8 shows an example isochrone map. A wave is propagating from a circle 810 with an x inside. Each circle represents time of arrival in milliseconds (msec) according to a shaded-bar. One or more circles 830 represent location of electrodes, with a number therein representing an estimation error in msec.

According to one or more embodiments, the generation engine 101 can modify the above model base DOA with respect to dimensionality reduction, weighted DOA estimation, and/or DOA Iterative mode.

Regarding dimensionality reduction, the catheter 14 can be projected to a surface. Projection is performed by the generation engine 101 taking two eigen vectors with highest eigen values. If energy preserved by the two eigenvalues is greater than 95%, then the generation engine 101 assumes/determines that a projection from 3D space to a surface is valid with respect to $\theta=(x_0, y_0, z_0, t_0, v)$, without the z dimension, as shown by Equations 8-13.

$$J(\theta) = \frac{1}{m}\sum_{i=m}^{m}(v\cdot d_i + t_0 - t_i)^2 + \frac{\lambda}{2m}\left(x_0^2 + y_0^2 + \frac{1}{v^2}\right) \qquad \text{EQUATION 8}$$

$$d_i = \sqrt{(x_i - x_0)^2 + (y_i - y_0)^2} \qquad \text{EQUATION 9}$$

$$\frac{\partial J(\theta)}{\partial x_0} = -\frac{2}{m}\sum_{i=m}^{m}\frac{(v\cdot d_i + t_0 - t_i)}{d_i}(x_i - x_0) + \frac{\lambda\cdot X_0}{m} \qquad \text{EQUATION 10}$$

$$\frac{\partial J(\theta)}{\partial y_0} = -\frac{2}{m}\sum_{i=m}^{m}\frac{(v\cdot d_i + t_0 - t_i)}{d_i}(y_i - y_0) + \frac{\lambda\cdot y_0}{m} \qquad \text{EQUATION 11}$$

27

-continued $$\frac{\partial J(\theta)}{\partial v} = \frac{2}{m}\sum\nolimits_{i=m}^{m}(v \cdot d_i + t_0 - t_i) \cdot d_i + \frac{\lambda}{m \cdot v^3}$$   EQUATION 12

$$\frac{\partial J(\theta)}{\partial t_0} = \frac{2}{m}\sum\nolimits_{i=m}^{m}(v \cdot d_i + t_0 - t_i)$$   EQUATION 13

Figure 9:
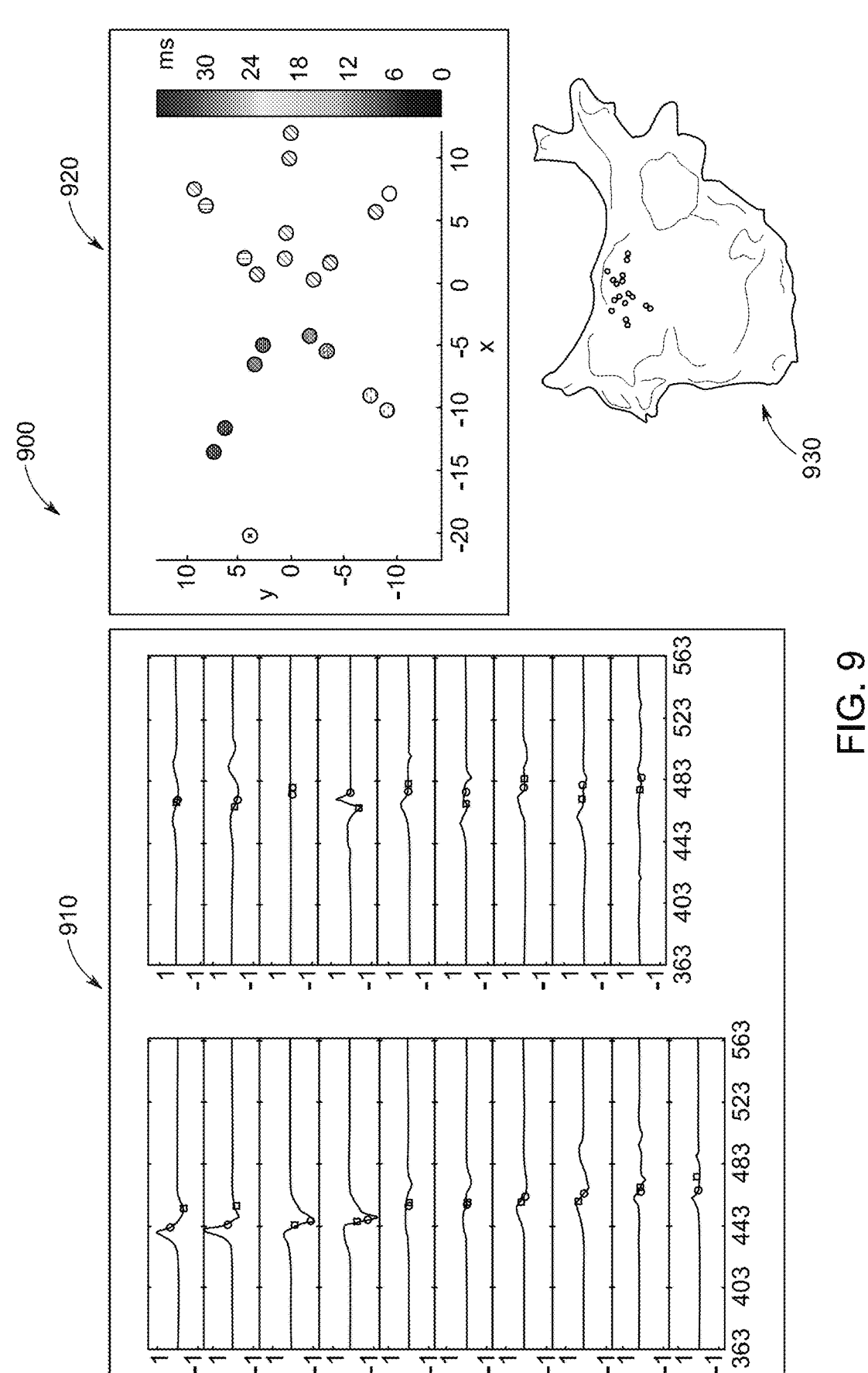
FIG. 9 illustrates an interface according to one or more embodiments.

Turning now to FIG. 9, the interface 900 is shown according to one or more embodiments. The interface 900 relates to an example of 2D DOA estimation (where 97.7% of the energy is preserved so a 2D DOA estimation is applied). A first portion 910 of the interface 900 provides unipolar signals sorted based on $t_i$, where the rectangles represents estimated $t_i$ based on estimation of $x_0$, $y_0$, $z_0$, $t_0$, and v. In the example shown by interface 900, a single wave traveling toward the catheter 14. An upper FIG. 920 of the interface 900 depicts the estimated focal activity (circle with x inside). The circles represent location of electrodes in X-Y space. An lower FIG. 930 of the interface 900 represents the actual location of the catheter 14 on the anatomy of the left atria.

Regarding Weighted DOA estimation, the generation engine 101 provides a "sharp" activation that is more "reliable" than a shallow activation, where a level of sharpness can be defined based dv/dt of the unipolar signal at $t_i$. Each $t_i$ can be mapped to a weight between 0 to 1 based on a corresponding dv/dt. An alternation can be set for the 2D according to equations 14-18.

$$J(\theta) = \frac{1}{m}\sum\nolimits_{i=m}^{m} w_i \cdot (v \cdot d_i + t_0 - t_i)^2 + \frac{\lambda}{2m}\left(x_0^2 + y_0^2 + \frac{1}{v^2}\right)$$   EQUATION 14

$$\frac{\partial J(\theta)}{\partial x_0} = -\frac{2}{m}\sum\nolimits_{i=m}^{m}\frac{w_i \cdot (v \cdot d_i + t_0 - t_i)}{d_i}(x_i - x_0) + \frac{\lambda \cdot x_0}{m}$$   EQUATION 15

$$\frac{\partial J(\theta)}{\partial y_0} = -\frac{2}{m}\sum\nolimits_{i=m}^{m}\frac{w_i \cdot (v \cdot d_i + t_0 - t_i)}{d_i}(y_i - y_0) + \frac{\lambda \cdot y_0}{m}$$   EQUATION 16

$$\frac{\partial J(\theta)}{\partial v} = \frac{2}{m}\sum\nolimits_{i=m}^{m} w_i \cdot (v \cdot d_i + t_0 - t_i) \cdot d_i + \frac{\lambda}{m \cdot v^3}$$   EQUATION 17

$$\frac{\partial J(\theta)}{\partial t_0} = \frac{2}{m}\sum\nolimits_{i=m}^{m} w_i \cdot (v \cdot d_i + t_0 - t_i)$$   EQUATION 18

Figure 10:
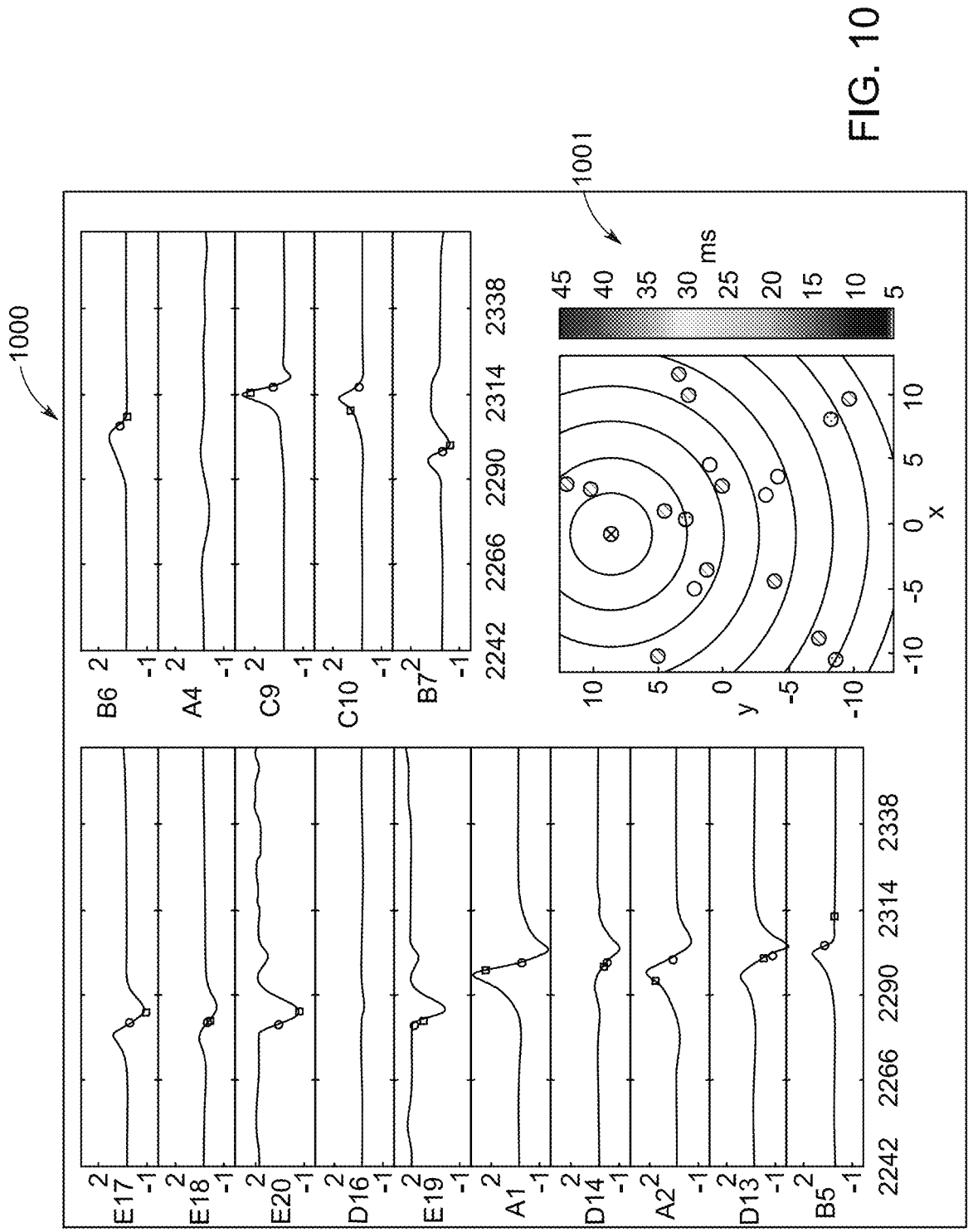
FIG. 10 illustrates an interface according to one or more embodiments.

Turning to FIG. 10, the interface 1000 is shown according to one or more embodiments. The interface 1000 is an example of a Weighted DOA that was detected as focal activity. The graphs of the interface 1100 provide signals respective to electrodes (e.g., B5, B7, D13, C10, etc.) In the interface 1000, notice that earliest S-wave pattern at electrodes E19 and E20. In a chart 1001 of the interface 1000, each circle can represent to a weight of a slope.

Regarding DOA Iterative mode, if an average estimation error is above a certain threshold (e.g., 7 msec), then the generation engine 101 enters an iterative mode for DOA estimation. In each iteration, a local activation time with highest estimation error is removed from the DOA estimation. The process can be repeated, while there are more than 10 valid local activation times.

Figure 11:
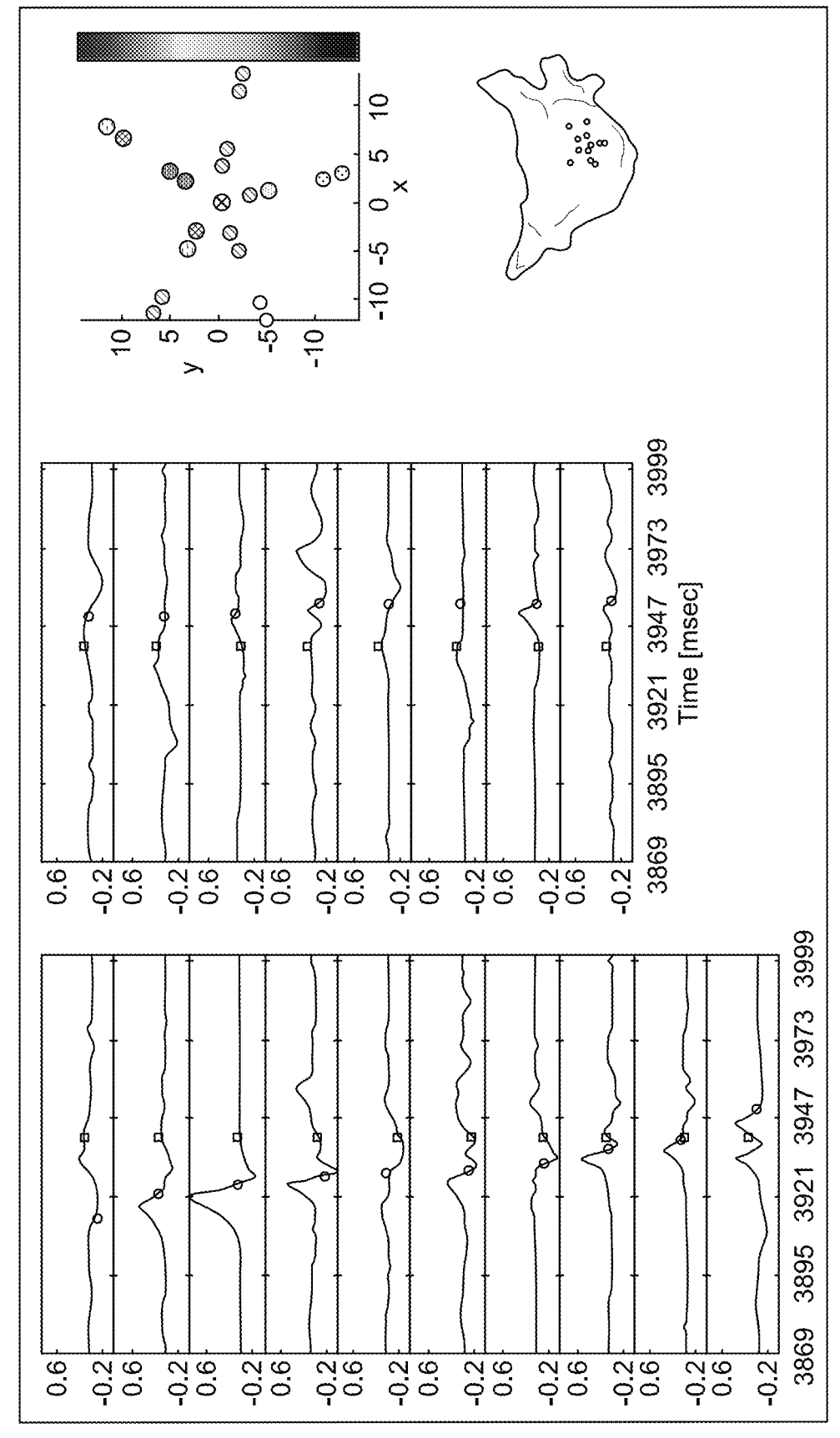
FIG. 11 illustrates an interface according to one or more embodiments.

Turning to FIG. 11, the interface 1100 is shown according to one or more embodiments. The interface is an example of how to display information respective to an estimation of focal activity in a center of the catheter 14. Note that due to a high estimation error of 12.4 msec, the generation engine 101 initiates an iterative mode. The graphs of the interface 1100 provide signals that represent a specific heart beat and activation time (i.e., a time that the signal passed bellow each pair of electrodes). A 3D image of the interface 1100 represents a location of each electrode in a left atria. A 2D image of the interface 1100 presented in a graph represents the position of each electrodes pair on the surface and the relative activation time.

Figure 12:
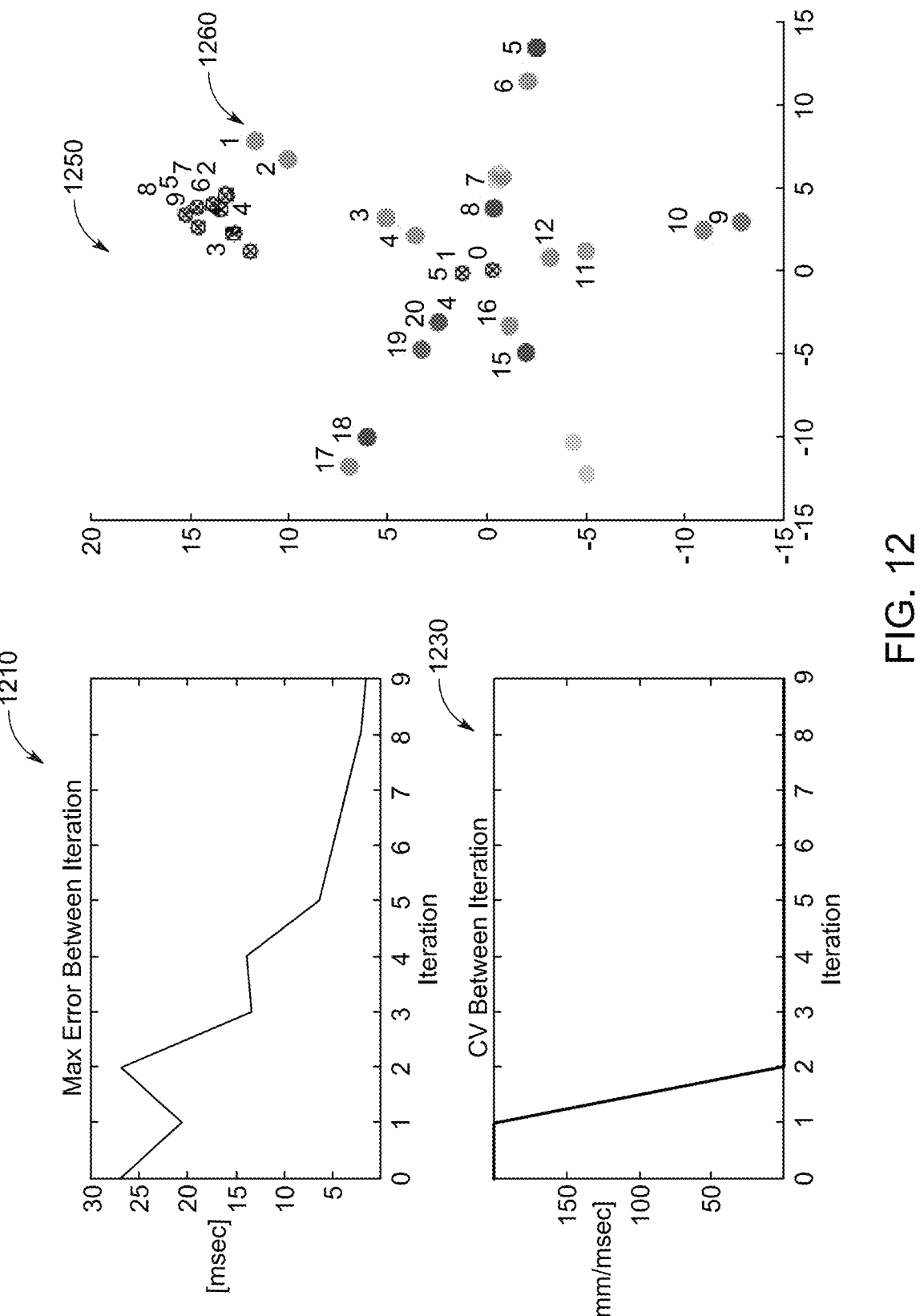
FIG. 12 illustrates graphs according to one or more embodiments.

Turning to FIG. 12, one or more graphs 1210, 1230, and 1250 are shown according to one or more embodiments. The one or more graphs 1210, 1230, and 1250 illustrate a first iteration of the focal source (e.g., at the center of the catheter 14), as well as second to ninth iterations of focal activity (e.g., which is shifted and placed near an electrode). The graph 1210 depicts a max error per iteration. The graph 1230 depicts a conduction velocity per iteration. Both graph 1210 and 1230 combine to show an overall convergence of the model to a "reasonable solution" (the maximum error dropped below 5 msec after the second iteration and the CV is 0.5 mm/msec). In graph 1250, dots 1260 represent valid electrodes for DOA estimation, electrodes represent invalid electrodes, and "iter 9" represent that this electrode was eliminated from DOA estimation at iteration 9. Note that the iterative model is used to handle cases of noisy local activation time or cases with more than one wave propagating toward the catheter 14.

Figure 13:
FIG. 13 illustrates an interface according to one or more embodiments.

Turning to FIG. 13, the interface 1300 shows an example of a DOA solution at iteration 9 (i.e., an actual results of the model). The graphs 1301 provide signals that represent a specific heart beat and activation time (i.e., a time that the signal passed bellow each pair of electrodes). A 3D image 1305 represents a location of each electrode in a left atria, and a 2D image 1310 presented in a graph represents the position of each electrodes pair on the surface and the relative activation time. According to one or more embodiments, the graphs 1301 unipolar signals after removing a far field activation (to dabble measured points). According to one or more embodiments, the signals can be procured by the catheter 14 having one or more splines and one or more electrodes per spline (e.g., an OCTARAY® mapping catheter with 48 electrodes). Estimation error of the model is an important quantity. Estimation error is a measure for a "goodness" of a fit of the model. When the final model yields an overall estimation error of above certain threshold (e.g., 7 msec), the generation engine 101 can assume that a segment is invalid for analysis. The percentage of invalid segments is a good measure for the "complexity" of the aFib in this subject. When using high density catheters and far field reduction algorithm, the "estimation error" can be calculated by the generation engine 101 per a group of electrodes or on a per electrode basis, where the "goodness" can be generated by each electrode.

Figure 14:
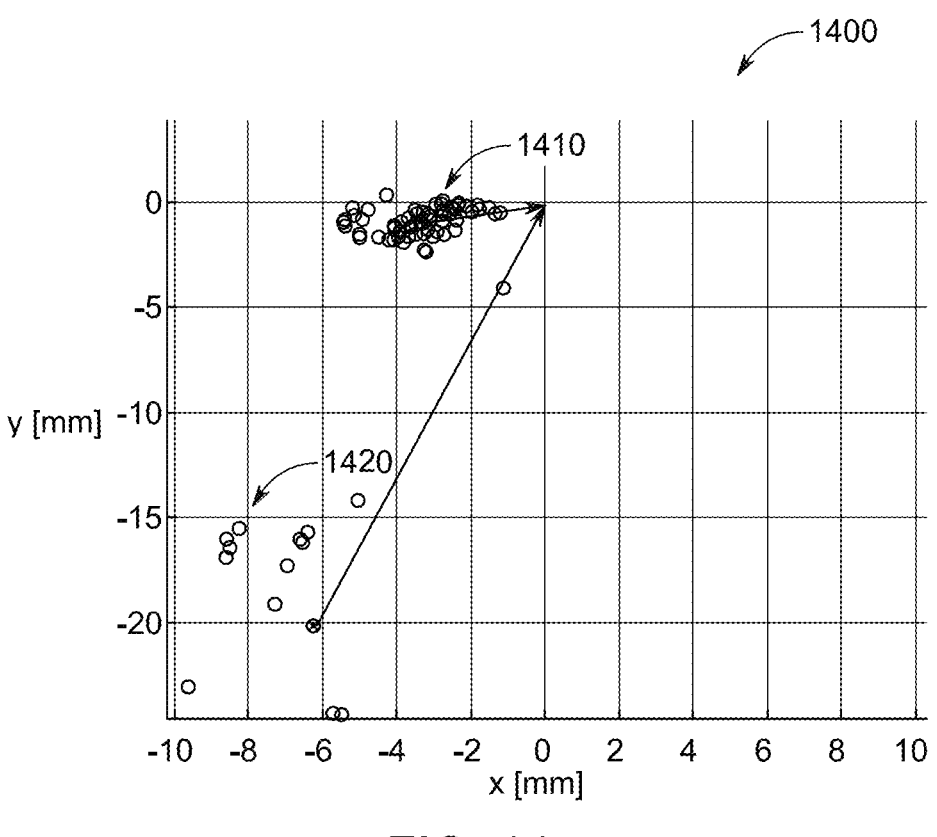
FIG. 14 illustrates a graph according to one or more embodiments.

With respect to the generation engine 101 moving from segment DOA to conduction velocity vectors, it is noted that the term DOA can represent the estimation of conduction velocity and (x, y) location of the wave that is propagating toward the catheter 14. As noted herein, the generation engine 101 can provide an estimation of conduction velocity vector single segment of local atrial activation. A segment duration is typically 100-200 msec. Further, a typical recording has 2.5-30 seconds of unipolar signals and contains approximately 10-200 segments during aFib. Therefore, all valid DOA are stored until all segments are processed and then a k-means clustering is performed. FIG. 14 and a graph 1400 depict an example of DOA clustering according to one or more embodiments. The generation engine 101 can execute a per recording based on clustering of DOA decision. Every circle represents DOA estimation from a segment of LAT within the recording. In this recording, there are two clusters of DOA that "explains" the data. The first cluster 1410 (circle at (−3.7 mm, −0.2 mm)) contains 80.5% of the DOAs, and the second cluster 1420 contains 19.5% of DOA in the recording. The output of the clustering is 1-3 typical CV vectors.

A focal source is detected, by the generation engine 101, if the dominant cluster falls within an 8 mm radius from the center of the catheter 14. A focal source may also be validated if at least 10 indications (configurable) of earliest S-wave patterns are found in electrodes located within a radius of 8 mm from the focal. Note that foci detection based DOA could manifested in location on the anatomy without placing a catheter in the focal activity therefore the validation process is optional.

Figure 15:
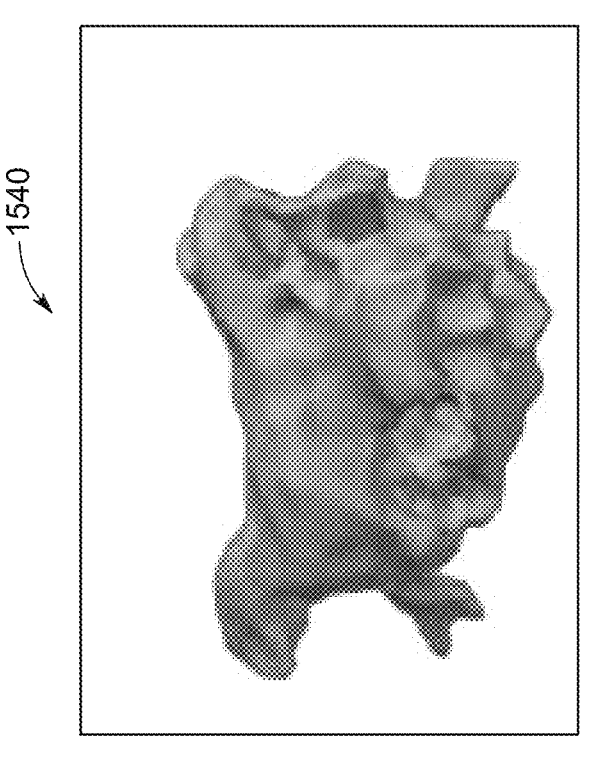
FIG. 15 illustrates interfaces according to one or more embodiments.
Figure 15:
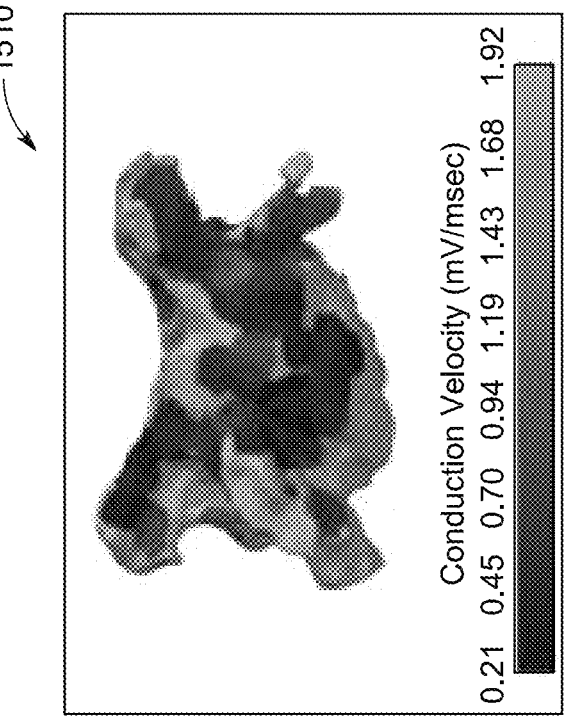

FIG. 15 illustrates interfaces 1510 and 1540 according to one or more embodiments. The interface illustrate 1510 focal map. The interface 1540 illustrate conduction velocity static map. The maps of interfaces 1510 and 1540 are based on DOA algorithm presented on the left atria.

According to one or more embodiments, a Lattice-Boltzmann Model for Electrical flows simulations is described. The bottom-up stage of DTA algorithm of the generation engine 101 outputs CV vectors and focal source location per points of electrophysiology measurements, i.e., locations of measurements with PentaRay® catheter. The last stage of the algorithms of the generation engine 101 uses Lattice Boltzmann Model for estimating patterns of electrical flows simulations based on conduction velocity vectors. The atria are voxelated into K voxels and each voxel sees only its six immediate nearest neighbors. A measurement from previous stage is used to assign a set of possible conduction velocity vectors to each voxel. See Equation 19, where Øv represents M conduction velocity vectors associated with the voxel v. |ø_{ζ,i}| is the actual conduction velocity in V/sec and Ø_{ix}, Ø_{iy} is their x and y components.

$$\emptyset v = \begin{vmatrix} |\emptyset_1| & \emptyset_{1x} & \emptyset_{1y} \\ \vdots & \vdots & \vdots \\ |\emptyset_M| & \emptyset_{Mx} & \emptyset_{My} \end{vmatrix} \quad \text{EQUATION 19}$$

For each time sample t, the generation engine 101 estimate per voxel the probability for an activation subject to the constraints of conduction velocity, cycle length and boundaries conditions. The generation engine 101 can assume that every voxel with bipolar voltage value below 0.5 mV is nonconductive and that the wave is restricted from activating this voxel. One or more boundary conditions could also be assumed, by the generation engine 101, based on ablation points or ablation line given as an input to the algorithm from a user that is trying to simulate the best ablation approach. The generation engine 101 initiates operations/algorithms when the dominant voxel with focal source indication is "firing" at time 0. If there are none, focal sources are initiated based on clinical assumptions. For example, the generation engine 101 selects the Buchman bundle as the focal source location since it is the preferential path for electrical activation of the left atria during normal sinus rhythm.

The generation engine 101 determines/calculates a probability for seeing an activation wave in the immediate neighbors of the focal, according to Equation 20.

$$f(v + e_i, t - dt) = \begin{cases} 1 & \text{if } CV \text{ criterion, no Scar} \\ 0 & \text{else} \end{cases} \quad \text{EQUATION 20}$$

$e_i$ represents one of the 7 immediate nearest neighbors and dt is 1 msec in the system. If f(x+e_i,t+dt)=1, the generation engine 101 estimates current CV of x+e_i (e.g., several methods can be applied by the generation engine 101, such as collect information of the wave in the vicinity of voxel x+e_i in the last 20 msec). Next, by denoted θ=[|θ|,θ_k,θ_y] as the estimated CV associated with voxel x+e_i, then the CV criterion can be defined according to Equations 21-23.

$$CV \text{ criterion 1: } \frac{|\theta|}{\theta_i} < 0.01 \cdot \alpha \quad \text{EQUATION 21}$$

$$CV \text{ criterion 2: } \frac{|\theta_i|}{\theta} < 0.01 \cdot \alpha \quad \text{EQUATION 22}$$

$$\text{cosine similarity: } \frac{\theta_{ix} \cdot \theta_x + \theta_{iy} \cdot \theta_y}{|\theta||\theta_i|} > 1 - 0.01 \cdot \alpha \quad \text{EQUATION 23}$$

Figure 16:
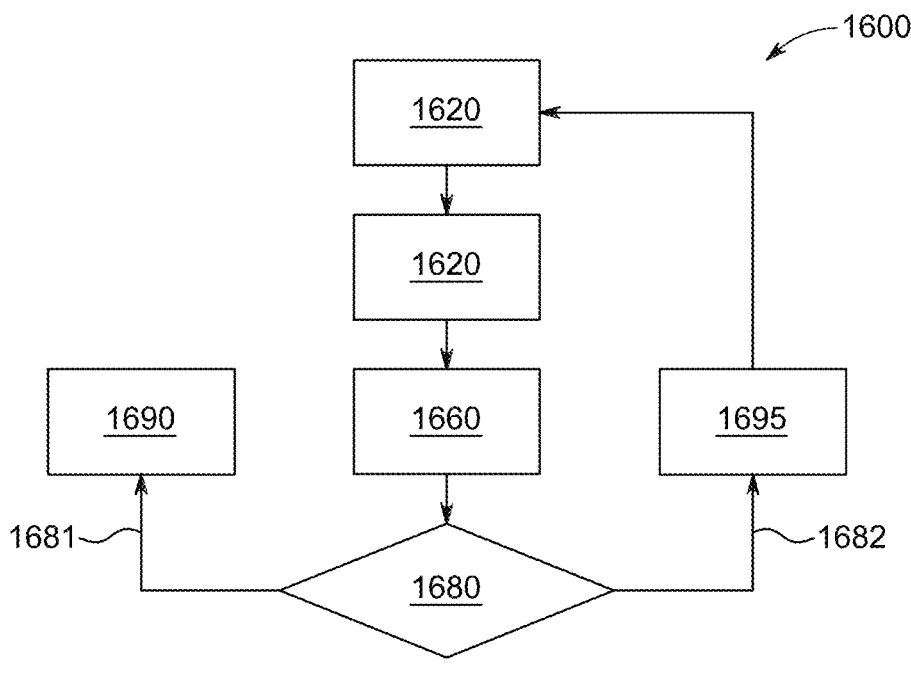
FIG. 16 illustrates a method according to one or more embodiments.

Note that α=1 at the beginning of the estimation and that α is increased by a factor of two every time the Lattice Boltzmann Model fails to estimate a wave. If, for a given expected CV sample θ_i, all the above criteria are met, then the CV velocity criteria is met and f(v+e_i,t+dt) is equal to 1 (e.g., and if v+e_i is not a scar voxel). In turn, the generation engine 101 can implement a modified Lattice Boltzmann Model according to FIG. 16 and method 1600.

The method 1600 begins at block 620, where the generation engine 101 voxelizes the atria set Øv for each voxel. At block 1640, the generation engine 101 sets an initial voxel of focal source.

Then, at block 1660, the generation engine 101 determines, for each t, t←t+dt. Further, at block 1660, for every voxel v, if v+e_i is a scar voxel f(v+e_i,t+dt)=0, break. Additionally, assume f(v,t)=1; estimate θ; if the CV criteria met for voxel v+e_i at time t+dt then f(v+e_i,t+dt)=1; if the CV criteria is not met, then f(v+e_i,t+dt)=0.

At decision block 1680, the generation engine 101 determines whether there is a valid wave. If so, the method 400 proceeds to block 1690 (as shown by the 1681 arrow), where the generation engine 101 utilizes a same α for the estimation (e.g., note that α=1 at the beginning of the estimation). Otherwise, the method 400 proceeds to block 1695 (as shown by the NO arrow), where the generation engine 101 increases α and re-estimates with the higher α return. As noted herein, α can be increased by a factor of two every time the Lattice Boltzmann Model fails to estimate a wave (e.g., α, (α=α·2).

Regarding implementation, the generation engine 101 considers the CV for defining the overall firing rate of the focal source. Further, once a typical wave is estimated for a single cycle, the matrix Øv can be into two different matrices. For example, a first matrix can include only elements of Øv that met the conduction CV criteria, and a second matrix can include elements that did not meet the CV criteria. The second matrix can be used to create second simulation of the wave in aFib.

According to one or more embodiments, a digital twin of atria for an aFib patient can be a robust computer generated replica of the atria with personalized electrical activity to serve as a guiding tool for ablations. To generate and create the digital twin, the generation engine measures and utilizes the personalized electrical activity of the heart and CV vectors, while accounting for arrhythmia triggers and information regarding atrial wall substances. Then, during an ablation procedure, the generation engine continuous updates the digital twin, as well as suggest an optimal ablation and/or additional procedures based on the digital twin. As a result, the digital twin generated by the generation engine is very accurate compared to current digital simulations and can be used for effective guidance during ablation procedures by cardiac physicians and medical personnel.

According to one or more advantages and technical benefits, the generation engine 101 and the ADT can simulate different ablation approaches and select an approach that reduces the arrhythmia with minimum area of ablation. According to one or more advantages and technical benefits, the generation engine 101 updates, for each ablation line, a "scar" matrix and creates a simulation based on new boundaries. According to one or more advantages and technical benefits, the generation engine 101 provides/supports successful ablation approaches by reducing a duration of activation period with respect to atria cycle length. According to one or more advantages and technical benefits, the generation engine 101 and the model simulate interaction between focal activities to determine which of the focal are more important for ablation.

According to one or more embodiments, a method is provided. The method enables an improved understanding an electrophysiology of an anatomical structure with precision via a digital twin. The method is implemented by a generation engine executed by one or more processors. The method includes receiving one or more inputs. The one or more inputs include one or more images and conduction velocity vector estimations. The method includes generating the digital twin of the anatomical structure utilizing the one or more images and the conduction velocity vector estimations. The method includes presenting the digital twin in a user interface acting a guiding tool for a medical procedure.

According to one or more embodiments or any of the method embodiments herein, the one or more inputs can include baseline recordings, the conduction velocity vector estimations, or a lattice Boltzmann model for simulating typical waves propagating along the anatomical structure.

According to one or more embodiments or any of the method embodiments herein, the digital twin can be based on the baseline recordings, the conduction velocity vector estimations, or the lattice Boltzmann model.

According to one or more embodiments or any of the method embodiments herein, the digital twin can be generated to determine how the electricity flows through that anatomy based on performing one or more of a direction of arrival estimation, a clustering, a voxelizing, and dynamic three-dimensional generation.

According to one or more embodiments or any of the method embodiments herein, the DOA estimations can automatically identify the conduction velocity vectors estimations of arrhythmogenic activity from intracardiac electrocardiogram or body surface electrocardiogram.

According to one or more embodiments or any of the method embodiments herein, the user interface can provide one or more simulations with respect to the digital twin showing how electricity flows through the anatomical structure based on a best conduction velocity vector.

According to one or more embodiments or any of the method embodiments herein, the medical procedure can include at least an ablation procedure.

According to one or more embodiments or any of the method embodiments herein, the anatomical structure can include atria of a heart.

According to one or more embodiments or any of the method embodiments herein, the one or more inputs comprise patient specific data.

According to one or more embodiments or any of the method embodiments herein, the generation engine can receive one or more additional inputs.

According to one or more embodiments or any of the method embodiments herein, the generation engine can generate one or more different ablation approaches and suggestions for the medical procedure.

According to one or more embodiments or any of the method embodiments herein, the generation engine can execute a remapping operation of the digital twin based on the one or more additional inputs.

According to one or more embodiments or any of the method embodiments herein, the generation engine can generate a digital twin local activation times map based on a digital twin model.

According to one or more embodiments or any of the method embodiments herein, the generation engine can update conduction velocity vector estimations of ablated cells in the digital twin model based on an ablation model that influenced the digital twin local activation times map.

According to one or more embodiments or any of the method embodiments herein, the digital twin can be generated for atrial fibrillation patients.

According to one or more embodiments, a method is provided. The method enables an improved understanding an electrophysiology of an anatomical structure with precision via an atrial digital twin of an atrial of a heart. The method is implemented by a generation engine executed by one or more processors. The method includes generating the atrial digital twin utilizing one or more images and conduction velocity vector estimations and presenting the atrial digital twin in a user interface acting a guiding tool for a medical procedure. The method also includes simulating one or more different ablation approaches across the atrial digital twin and selecting an approach from the one or more different ablation approaches that reduces an arrhythmia with a minimum area of ablation.

According to one or more embodiments, a method is provided. The method enables an improved understanding an electrophysiology of an anatomical structure with precision via an atrial digital twin of an atrial of a heart. The method is implemented by a generation engine executed by one or more processors. The method includes generating the atrial digital twin utilizing one or more images and conduction velocity vector estimations and presenting the atrial digital twin in a user interface acting a guiding tool for a medical procedure. The method also includes simulating one or more interactions between focal activities with respect to the atrial digital twin and determining a foci based on the one or more interactions that is most important for ablation.

The flowchart and block diagrams in the Figures illustrate the architecture, functionality, and operation of possible implementations of systems, methods, and computer program products according to various embodiments of the present invention. In this regard, each block in the flowchart or block diagrams may represent a module, segment, or portion of instructions, which comprises one or more executable instructions for implementing the specified logical function(s). In some alternative implementations, the functions noted in the blocks may occur out of the order noted in the Figures. For example, two blocks shown in succession may, in fact, be executed substantially concurrently, or the blocks may sometimes be executed in the reverse order, depending upon the functionality involved. It will also be noted that each block of the block diagrams and/or flowchart illustration, and combinations of blocks in the block diagrams and/or flowchart illustration, can be implemented by special purpose hardware-based systems that perform the specified functions or acts or carry out combinations of special purpose hardware and computer instructions.

Although features and elements are described above in particular combinations, one of ordinary skill in the art will appreciate that each feature or element can be used alone or in any combination with the other features and elements. In addition, the methods described herein may be implemented in a computer program, software, or firmware incorporated in a computer-readable medium for execution by a computer or processor. A computer readable medium, as used herein, is not to be construed as being transitory signals per se, such as radio waves or other freely propagating electromagnetic waves, electromagnetic waves propagating through a waveguide or other transmission media (e.g., light pulses passing through a fiber-optic cable), or electrical signals transmitted through a wire Examples of computer-readable media include electrical signals (transmitted over wired or wireless connections) and computer-readable storage media. Examples of computer-readable storage media include, but are not limited to, a register, cache memory, semiconductor memory devices, magnetic media such as internal hard disks and removable disks, magneto-optical media, optical media such as compact disks (CD) and digital versatile disks (DVDs), a random access memory (RAM), a read-only memory (ROM), an erasable programmable read-only memory (EPROM or Flash memory), a static random access memory (SRAM), and a memory stick. A processor in association with software may be used to implement a radio frequency transceiver for use in a terminal, base station, or any host computer.

The terminology used herein is for the purpose of describing particular embodiments only and is not intended to be limiting. As used herein, the singular forms "a", "an" and "the" are intended to include the plural forms as well, unless the context clearly indicates otherwise. It will be further understood that the terms "comprises" and/or "comprising," when used in this specification, specify the presence of stated features, integers, steps, operations, elements, and/or components, but do not preclude the presence or addition of one more other features, integers, steps, operations, element components, and/or groups thereof.

The descriptions of the various embodiments herein have been presented for purposes of illustration, but are not intended to be exhaustive or limited to the embodiments disclosed. Many modifications and variations will be apparent to those of ordinary skill in the art without departing from the scope and spirit of the described embodiments. The terminology used herein was chosen to best explain the principles of the embodiments, the practical application or technical improvement over technologies found in the marketplace, or to enable others of ordinary skill in the art to understand the embodiments disclosed herein.

What is claimed is:

1. An ablation procedure guidance method, for improving intra-procedural mapping accuracy and ablation efficacy by generating and validating a patient-specific electrophysiology digital twin and using it to parameterize energy delivery, implemented by one or more processors, the method comprising:

receiving, by the one or more processors, inputs comprising (i) intracardiac electrogram signals acquired from a multi-electrode intracardiac catheter at known electrode positions and (ii) one or more images registered to a three-dimensional atrial geometry;

estimating, by the one or more processors, direction-of-arrival values from the intracardiac electrogram signals at surface sample points of the atrial geometry by computing time-of-arrival differences across electrode neighborhoods within a time window of interest;

computing, by the one or more processors, conduction velocity vector estimations as a vector field over the atrial geometry by fitting the vector field to direction-of-arrival values derived from the intracardiac electrogram signals and regularizing the fitted vector field to satisfy smoothness and physiological-conduction constraints across the atrial surface;

generating, by the one or more processors, a digital twin of an anatomical structure using the one or more images and the conduction velocity vector estimations;

performing, by the one or more processors, a forward activation-propagation simulation on the digital twin to generate local activation time values;

validating, by the one or more processors, the digital twin by comparing the local activation time values to corresponding measured values and accepting the digital twin when a estimation error satisfies a tolerance;

generating, by the one or more processors, an ablation procedure guidance plan comprising: lesion locations on the atrial surface, a delivery sequence, and energy-delivery parameters;

transmitting, by the one or more processors, control signals encoding the energy-delivery parameters to an ablation generator for execution of an ablation procedure according to the delivery sequence; and presenting, via a user interface of the generation engine, the digital twin with overlaid conduction-velocity vectors and local activation time maps to provide precision ablation guidance and electrophysiology information of the anatomical structure.

2. The ablation procedure guidance method of claim 1, wherein the inputs further comprise baseline recordings of intracardiac electrogram signals or a lattice Boltzmann model.

3. The ablation procedure guidance method of claim 1, estimating the direction-of-arrival values further comprises rejecting outlier time-of-arrival differences that fail a quality threshold within the time window of interest.

4. The ablation procedure guidance method of claim 1, wherein the one or more inputs further comprise arrhythmogenic activity from the intracardiac electrocardiogram or a body surface electrocardiogram.

5. The ablation procedure guidance method of claim 1, computing the conduction velocity vector field further comprises applying model constraints that incorporate conduction criteria and non-conductive boundary conditions corresponding to scar ablated tissue.

6. The ablation procedure guidance method of claim 1, wherein the precision ablation guidance includes simulating how electricity flows through the digital twin based on the conduction velocity vector estimations and determining whether a targeted propagation pathway is interrupted.

7. The ablation procedure guidance method of claim 1, further comprising receiving one or more additional inputs during the ablation procedure and, in response, generating different ablation procedure guidance or performing a remapping operation of the digital twin.

8. The ablation procedure guidance method of claim 1, further comprising generating a digital-twin local activation time map based on a digital-twin model, and updating conduction velocity vector estimations of lesioned surface elements in the digital-twin model according to an ablation model and re-simulating activation propagation to confirm termination of a targeted pathway.

9. The ablation procedure guidance method of claim 1, wherein the precision ablation guidance includes simulating interactions between focal activities with respect to the digital twin and determining one or more foci for ablation based on the one or more interactions.

10. The ablation procedure guidance method of claim 1, wherein the anatomical structure comprises atria of a heart, and wherein the inputs comprise patient-specific data acquired intra-procedurally.

11. A system for improving intra-procedural mapping accuracy and ablation efficacy by generating and validating a patient-specific electrophysiology digital twin and using it to parameterize energy delivery, comprising:

a multi-electrode intracardiac catheter;

an imaging subsystem configured to provide a three-dimensional atrial geometry registered to electrode positions;

an ablation generator configured to deliver therapeutic energy;

one or more processors; and non-transitory computer readable memory storing instructions that, when executed by the one or more processors, cause the system to:

receive inputs comprising images and intracardiac electrogram signals from the catheter and the three-dimensional atrial geometry from the imaging subsystem;

estimate direction-of-arrival values at surface sample points by computing time-of-arrival differences across electrode neighborhoods within a time window of interest;

compute conduction velocity vector estimations as a vector field over the atrial geometry by fitting the vector field to direction-of-arrival values derived from the intracardiac electrogram signals and regularizing the fitted vector field to satisfy smoothness and physiological-conduction constraints across the atrial surface;

generate a digital twin of an anatomical structure using the one or more images and the conduction velocity vector estimations;

perform forward activation-propagation simulation on the digital twin to generate local activation time values;

validate the digital twin against measured local activation time values by accepting the digital twin when a estimation error satisfies a tolerance;

generate an ablation procedure guidance plan comprising: lesion locations, a delivery sequence, and energy-delivery parameters;

transmit control signals encoding the energy-delivery parameters to the ablation generator for execution of an ablation procedure according to the delivery sequence;

and present, via a user interface, the digital twin with overlaid conduction-velocity vectors and local activation time maps to provide precision ablation guidance and electrophysiology information.

12. The system of claim 11, wherein the one or more inputs comprise the one or more images, the conduction velocity vector estimations, and further comprise baseline recordings of intracardiac electrogram signals or a lattice Boltzmann model.

13. The system of claim 11, wherein estimating direction-of-arrival values further comprises rejecting outlier time-of-arrival differences that fail a quality threshold within the time window of interest.

14. The system of claim 11, validating the digital twin comprises accepting the digital twin when estimation error between simulated and measured local activation time values satisfies a tolerance.

15. The system of claim 11, wherein the ablation generator is a radiofrequency generator and the control signals specify at least one of power, or time.

16. The system of claim 11, wherein the ablation generator is a pulsed-field ablation generator and the control signals specify at least one of pulse amplitude, or pulse width.

17. The system of claim 11, wherein the instructions further cause the system to update direction-of-arrival estimation, conduction-velocity computation, forward simulation, validation, and the ablation plan intra-procedurally in response to newly acquired intracardiac electrogram signals.

18. The system of claim 11, wherein computing the conduction-velocity vector field further comprises applying model constraints that incorporate conduction criteria and non-conductive boundary conditions corresponding to scar or ablated tissue.

19. The system of claim 11, wherein the instructions further cause the system to update conduction-velocity vector estimations of lesioned surface elements in the digital-twin model according to an ablation model and to re-simulate activation propagation to confirm interruption of a targeted pathway.

*     *     *     *     *